United States Patent
Gabin et al.

(10) Patent No.: US 11,925,699 B2
(45) Date of Patent: Mar. 12, 2024

(54) GELLED COMPOSITION COMPRISING A DISPERSION OF SOLID AGGREGATES

(71) Applicant: L'OREAL, Paris (FR)

(72) Inventors: Philippe Gabin, Chevilly la Rue (FR); Celine Moussay, Chevilly la Rue (FR); Magali Szestak, Chevilly la Rue (FR)

(73) Assignee: L'OREAL, Paris (FR)

( * ) Notice: Subject to any disclaimer, the term of this patent is extended or adjusted under 35 U.S.C. 154(b) by 440 days.

(21) Appl. No.: 16/627,020

(22) PCT Filed: Jun. 26, 2018

(86) PCT No.: PCT/EP2018/067143
§ 371 (c)(1),
(2) Date: Dec. 27, 2019

(87) PCT Pub. No.: WO2019/002311
PCT Pub. Date: Jan. 3, 2019

(65) Prior Publication Data
US 2020/0222288 A1    Jul. 16, 2020

(30) Foreign Application Priority Data
Jun. 27, 2017 (FR) ...................................... 1755889

(51) Int. Cl.
| A61K 8/891 | (2006.01) |
| A61K 8/02 | (2006.01) |
| A61K 8/04 | (2006.01) |
| A61K 8/895 | (2006.01) |
| A61K 8/92 | (2006.01) |

(52) U.S. Cl.
CPC ............ *A61K 8/042* (2013.01); *A61K 8/0241* (2013.01); *A61K 8/891* (2013.01); *A61K 8/895* (2013.01); *A61K 8/927* (2013.01); *A61K 2800/10* (2013.01); *A61K 2800/412* (2013.01)

(58) Field of Classification Search
CPC .......... A61K 9/02; A61K 9/025; A61K 9/042; A61K 9/891; A61K 9/89; A61K 9/0241
See application file for complete search history.

(56) References Cited

U.S. PATENT DOCUMENTS

| 2015/0098973 A1* | 4/2015 | Brissette | ................ | A61K 8/922 |
| | | | | 424/59 |
| 2016/0000663 A1* | 1/2016 | Valverde | .................. | A61K 8/89 |
| | | | | 424/78.03 |
| 2016/0008236 A1* | 1/2016 | Valverde | ................ | A61K 8/042 |
| | | | | 514/777 |
| 2017/0189278 A1* | 7/2017 | Bchir | ..................... | A61K 8/891 |

FOREIGN PATENT DOCUMENTS

| BR | PI0405758 A | 9/2006 |
| JP | 2005-112834 A | 4/2005 |
| WO | 99/632497 A1 | 12/1999 |
| WO | 9965455 A1 | 12/1999 |
| WO | 2008/081175 A2 | 7/2008 |
| WO | 2015/181733 | * 12/2015 |
| WO | 2016030841 A2 | 3/2016 |
| WO | 2016083385 A1 | 6/2016 |

OTHER PUBLICATIONS

International Search Report (ISR) for PCT/EP2018/067143 dated Sep. 3, 2018 (3 pages).
Written Opinion of the International Searching Authority for PCT/EP2018/067143 dated Sep. 3, 2018 (5 pages).
I.F. Almeida et al., "Moisturizing Effect of Oleogel/Hydrogel Mixtures", Pharmaceutical Development and Technology, vol. 13, p. 487-494, (2008).

* cited by examiner

*Primary Examiner* — Margaret G Moore
(74) *Attorney, Agent, or Firm* — Shumaker, Loop & Kendrick, LLP

(57) ABSTRACT

A composition, especially a cosmetic composition, in particular for making up and/or caring for keratin materials, including at least one aqueous phase gelled with at least one hydrophilic gelling agent; and at least one oily phase gelled with at least one lipophilic gelling agent chosen from organopolysiloxane elastomers; said phases forming therein a macroscopically homogeneous mixture. The composition also includes a dispersion of solid aggregates, said aggregates being formed from 10% to 80% by weight of wax(es), relative to their total weight. Also disclosed is a process for preparing such a composition.

12 Claims, No Drawings

GELLED COMPOSITION COMPRISING A DISPERSION OF SOLID AGGREGATES

TECHNICAL FIELD AND BACKGROUND

The present invention is directed towards proposing for the field of caring for and hygiene of keratin materials, especially the skin and/or the lips, and in particular the skin, a novel galenical form that is most particularly advantageous with regard to its technical performance and the sensations it affords the user during its application thereto, in particular to the skin.

The term "keratin materials" especially means the skin, the lips and/or the eyelashes, in particular the skin and/or the lips, and preferably the skin.

Cosmetic compositions are commonly used to hide and/or unify imperfections of the skin relief such as pores, wrinkles and/or fine lines and/or scars. In this regard, many solid or fluid, anhydrous or non-anhydrous formulations have been developed to date.

When these compositions are more particularly intended for attenuating the visibility of the skin's relief, the formulator uses diffusing fillers or soft-focus fillers. However, the corresponding compositions that are currently available do not prove to be entirely satisfactory especially in terms of soft-focus performance.

In order to obtain a satisfactory degree of soft focus, it is often necessary to introduce a large amount of soft-focus fillers into the composition. However, this content of soft-focus fillers may lead to destabilization of said composition and lead to cosmetic properties that are not in accordance with the users' expectations, especially the formation of fluffing during the application of the product and/or after drying and/or penetration of the product into the skin.

This defect is off-putting for users, since the application is not uniform or pleasant, given this fluffing effect on application or during removal of the product. In addition, it gives a "dirty" impression on the skin In order to overcome this problem and to afford comfortable care with a soft-focus effect, alternative oily presentation forms are currently proposed on the cosmetic market.

However, these formulations have drawbacks associated with the presence of large contents of fatty phase in the composition, i.e. producing shiny skin and/or the sensation of greasy and/or tacky skin.

The use of crosslinked silicones is another alternative. Specifically, starting materials of this type make it possible to combine a matt effect and a soft-focus effect. However, they have the drawback of being characterized by an uncomfortable hot and greasy feel, with a "mask" effect.

On another hand, a cosmetic composition combining a matt effect and a soft focus effect, comprising a hydroalcoolic or aqueous gel of synthetic phyllosilicate of formula $Mg_3Si_4O_{10}(OH)_2$, has already been proposed, such as in patent application No. WO 2016/083385.

Those phyllosilicates are in the form of platelets, consisting in an unique material, and dispersed in the aqueous phase.

However, these mineral compounds have the tendency to induce fluffing effect during application on the keratin materials when implemented in a cosmetic composition.

It thus remains difficult for a person skilled in the art to be able to develop homogeneous compositions that are capable of affording an immediate visual result on the skin with a sensation of lightness and comfort on application, with a non-tacky deposit and no fluffing effect during application, this expected immediate result preferentially being good coverage of colour imperfections and/or relief imperfections.

There is thus still a need for cosmetic compositions for hiding skin imperfections, while at the same time having good cosmetic properties, in particular in terms of optical and sensory effects.

SUMMARY

The present invention is directed precisely towards meeting this need.

Thus, according to one of its aspects, the present invention relates to a composition, especially a cosmetic composition, in particular for making up and/or caring for keratin materials, comprising:

at least one aqueous phase gelled with at least one hydrophilic gelling agent; and at least one oily phase gelled with at least one lipophilic gelling agent chosen from organopolysiloxane elastomers;

said phases forming therein a macroscopically homogeneous mixture;

characterized in that said composition also comprises a dispersion of solid aggregates, said aggregates being formed from 10% to 80% by weight of wax(es), relative to their total weight.

Contrary to all expectation, the inventors observed that the incorporation of a dispersion of solid aggregates as defined above makes it possible to improve the optical and sensory performance qualities of a composition of gel-gel architecture.

As emerges from the examples given below, the compositions according to the invention have better sensory qualities in terms of tack and glidance and also a better soft-focus optical effect.

Furthermore, the composition according to the present invention is particularly advantageous in that it exhibits a reduced fluffing effect or even no fluffing effect during the application.

"Gel-gel" compositions are already proposed in the cosmetics field. Formulations of this type combine a gelled aqueous phase with a gelled oily phase. Thus, gel/gel formulations are described in Almeida et al., Pharmaceutical Development and Technology, 2008, 13:487, tables 1 and 2, page 488; WO 99/65455; PI 0405758-9; WO 99/62497; JP 2005-112834 and WO 2008/081175. However, to the inventors' knowledge, this type of composition does not at the present time make it possible to conceal and smooth out relief imperfections without thereby impairing the other expected cosmetic performance qualities.

As mentioned above, the inventors found that the addition of a specific dispersion of solid aggregates in a composition of gel-gel type makes it possible to obtain a composition that combines optical and sensory performance qualities. In particular, a composition according to the invention makes it possible to mask imperfections and to afford a light complexion, while at the same time having good sensory properties, especially in terms of emollience, tack and glidance on the skin.

According to another of its aspects, a subject of the invention is also a process for preparing a composition according to the invention, comprising at least the following steps:

i) providing a first solid composition comprising from 10% to 80% by weight of wax(es), relative to the total weight of the composition;

ii) providing an oily phase gelled with at least one lipophilic gelling agent chosen from organopolysiloxane elastomers;

iii) mixing said first solid composition and said gelled oily phase with stirring at room temperature, under conditions that are effective for dispersing said first composition in the form of solid aggregates in said gelled oily phase;

iv) introducing into the mixture obtained on conclusion of the preceding step an aqueous phase gelled with at least one hydrophilic gelling agent, at room temperature, under conditions that are suitable for obtaining a macroscopically homogeneous mixture.

Preferably, in the preparation process according to the invention, said first solid composition of step i) is prepared at a temperature of between 30° C. and 120° C., preferably between 50° C. and 90° C., and then cooled to room temperature.

According to another of its aspects, a subject of the invention is also a cosmetic process for making up and/or caring for keratin materials, in particular the skin and/or the lips, comprising at least one step of applying a composition according to the invention to said keratin materials.

DETAILED DESCRIPTION

COSMETIC COMPOSITION To begin with, it is important to note that a composition according to the invention is different from an emulsion.

An emulsion is generally constituted by an oily liquid phase and an aqueous liquid phase. It is a dispersion of droplets of one of the two liquid phases in the other. The size of the droplets forming the dispersed phase of the emulsion is typically about a micrometre (0.1 to 100 μm). Furthermore, an emulsion requires the presence of a surfactant or of an emulsifier to ensure its stability over time.

In contrast, a composition according to the invention consists of a macroscopically homogeneous mixture of two immiscible gelled phases. These two phases both have a gel-type texture. This texture is especially reflected visually by a consistent and/or creamy appearance.

The term "macroscopically homogeneous mixture" means a mixture in which each of the gelled phases cannot be individualized by the naked eye.

More precisely, in a composition according to the invention, the gelled aqueous phase and the gelled oily phase interpenetrate and thus form a stable, consistent product. This consistency is achieved by mixing interpenetrated macrodomains. These interpenetrated macrodomains are not measurable objects. Thus, by microscope, the composition according to the invention is very different from an emulsion. A composition according to the invention cannot be characterized either as having a "sense", i.e. an O/W or W/O sense.

Thus, a composition according to the invention has a consistency of gel type. The stability of the composition is long-lasting without surfactant. Consequently, a composition, especially a cosmetic composition, according to the invention does not require any surfactant or silicone emulsifier to ensure its stability over time.

It is known practice from the prior art to observe the intrinsic nature of a mixture of aqueous and oily gels in a composition of gel type, for example, by introducing a dyestuff either into the aqueous gelled phase or into the lipophilic gelled phase, before the formation of the composition of gel type. During visual inspection, in a composition of gel type, the dyestuff appears uniformly dispersed, even if the dye is present solely in the gelled aqueous phase or in the gelled oily phase. Specifically, if two different dyes of different colours are introduced, respectively, into the oily phase and into the aqueous phase, before formation of the composition of gel type, the two colours may be observed as being uniformly dispersed throughout the composition of gel type. This is different from an emulsion in which, if a dye, which is soluble in water or soluble in oil, is introduced, respectively, into the aqueous and oily phases, before forming the emulsion, the colour of the dye present will only be observed in the outer phase (Remington: The Science and Practice of Pharmacy, 19th Edition (1995), Chapter 21, page 282).

In the case of the present invention, the test that will be preferred for distinguishing a composition of gel type from an emulsion is a dilution test. Specifically, in a composition of gel type, the aqueous and oily gelled domains interpenetrate and form a consistent and stable composition, in which the behaviour in water and in oil is different from the behaviour of an emulsion. Consequently, the behaviour during dilution of a composition of gel type (bi-continuous system) may be compared to that of an emulsion.

More specifically, the dilution test consists in placing 40 g of product and 160 g of dilution solvent (water or oil) in a 500 mL plastic beaker. The dilution is performed with controlled stirring to avoid any emulsification. In particular, this is performed using a planetary mixer: Speed Mixer TM DAC400FVZ. The speed of the mixer is set at 1500 rpm for 4 minutes. Finally, observation of the resulting sample is performed using a light microscope at a magnification of ×100 (×10×10). It may be noted that oils such as Parleam® and Xiameter PMX-200 Silicone Fluid 5CS® sold by Dow Corning are suitable as dilution solvent, in the same respect as one of the oils contained in the composition.

In the case of a composition of gel type (bi-continuous system), when it is diluted in oil or in water, a heterogeneous appearance is always observed. When a composition of gel type (bi-continuous system) is diluted in water, pieces of oily gel in suspension are observed, and when a composition of gel type (bi-continuous system) is diluted in oil, pieces of aqueous gel in suspension are observed.

In contrast, during dilution, emulsions have a different behaviour. When an O/W emulsion is diluted in an aqueous solvent, it gradually reduces without having a heterogeneous and lumpy appearance. This same O/W emulsion, on dilution with oil, has a heterogeneous appearance (pieces of O/W emulsion suspended in the oil). When a W/O emulsion is diluted with an aqueous solvent, it has a heterogeneous appearance (pieces of W/O emulsion suspended in the water). This same W/O emulsion, when diluted in oil, gradually reduces without having a heterogeneous and lumpy appearance.

According to the present invention, the aqueous gelled phase and the oily gelled phase forming a composition according to the invention are present therein in a weight ratio ranging from 95/5 to 5/95. More preferentially, the aqueous phase and the oily phase are present in a weight ratio ranging from 30/70 to 90/10.

The ratio between the two gelled phases is adjusted according to the desired cosmetic properties.

Thus, in the case of a makeup composition, in particular for the face, it will be advantageous to favour an aqueous gelled phase/oily gelled phase weight ratio of greater than 1, especially ranging from 55/45 to 90/10, preferably ranging from 60/40 to 85/15.

These preferred ratios are particularly advantageous for obtaining fresh and light compositions.

Advantageously, a composition according to the invention may thus be in the form of a creamy gel with a minimum stress below which it does not flow unless it has been subjected to an external mechanical stress.

As emerges from the text hereinbelow, a composition according to the invention may have a minimum threshold stress of 1.5 Pa and in particular greater than 10 Pa.

It may also advantageously have a stiffness modulus G* at least equal to 400 Pa and preferably greater than 1000 Pa.

According to an advantageous embodiment variant, the gelled phases under consideration to form a composition according to the invention may have, respectively, a threshold stress of greater than 1.5 Pa and preferably greater than 10 Pa.

Characterization of the threshold stresses is performed by oscillating rheology measurements. Methodology is proposed in the illustrative chapter of the present text.

In general, the corresponding measurements are taken at 25° C. using a Haake RS600 imposed-stress rheometer equipped with a plate-plate measuring body (60 mm diameter) fitted with an anti-evaporation device (bell jar). For each measurement, the sample is placed delicately in position and the measurements start 5 minutes after placing the sample in the jaws (2 mm). The test composition is then subjected to a stress ramp from $10^{-2}$ to $10^3$ Pa at a set frequency of 1 Hz.

A composition according to the invention may also have a certain elasticity. This elasticity may be characterized by a stiffness modulus G* which, under this minimum stress threshold, may be at least equal to 400 Pa and preferably greater than 1000 Pa. The value G* of a composition may be obtained by subjecting the composition under consideration to a stress ramp from $10^{-2}$ to $10^3$ Pa at a set frequency of 1 Hz.

Dispersion of Solid Aggregates

As mentioned previously, a composition according to the invention comprises at least one dispersion of solid aggregates.

According to a preferred embodiment, a composition according to the invention comprises from 1% to 40% by weight, preferably from 2% to 35% by weight and more preferentially from 5% to 30% by weight of solid aggregates relative to the total weight of the composition.

According to the invention, the term "aggregates" means an assembly of different compounds which adhere together and form a whole. Such aggregates may have varied shapes and sizes.

Preferably, the aggregates present in a composition according to the invention have a size of between 0.1 μm and 100 μm, preferably between 0.1 μm and 10 μm.

The term "solid" refers to aggregates or a composition having, at 25° C. and under atmospheric pressure (1 atm=105 Pa), a hardness of greater than 0.5 N, preferably greater than 2 N, said hardness preferably being measured using a texturometer equipped with a hemispherical probe 12.7 mm in diameter.

The term "dispersion of solid aggregates" means that the solid aggregates are dispersed in the composition according to the invention.

Preferably, the solid aggregates are dispersed in the gelled aqueous phase and/or in the gelled oily phase, and in particular predominantly in the gelled oily phase.

More preferentially, the aggregates are dispersed in the gelled oily phase.

Waxes

As indicated previously, the solid aggregates are formed from 10% to 80% by weight of wax(es), relative to their total weight.

Preferably, the solid aggregates are formed from 15% to 60% by weight of wax(es), preferably from 20% to 55% by weight of wax(es), relative to their total weight.

For the purposes of the present invention, the term "wax" means a lipophilic compound, which is solid at room temperature (25° C.), with a reversible solid/liquid change of state, having a melting point of greater than or equal to 30° C., which may be up to 120° C.

The melting point of the wax may be measured using a differential scanning calorimeter (DSC), for example the calorimeter sold under the name DSC 30 by the company Mettler.

Preferably, the measuring protocol is as follows:

A sample of 5 mg of wax placed in a crucible is subjected to a first temperature rise ranging from −20° C. to 100° C., at a heating rate of 10° C./minute, it is then cooled from 100° C. to −20° C. at a cooling rate of 10° C./minute and is finally subjected to a second temperature rise ranging from −20° C. to 100° C. at a heating rate of 5° C./minute. During the second temperature increase, the variation of the difference in power absorbed by the empty crucible and by the crucible containing the sample of wax is measured as a function of the temperature. The melting point of the compound is the temperature value corresponding to the top of the peak of the curve representing the variation in the difference in power absorbed as a function of the temperature.

The wax may especially have a hardness ranging from 0.05 MPa to 15 MPa and preferably ranging from 6 MPa to 15 MPa. The hardness is determined by measuring the compression force measured at 20° C. using a texturometer sold under the name TA-TX2i by the company Rheo, equipped with a stainless-steel cylinder 2 mm in diameter, travelling at a measuring speed of 0.1 mm/s, and penetrating the wax to a penetration depth of 0.3 mm.

The waxes may be hydrocarbon-based waxes, silicone or fluoro waxes, and may be of plant, mineral, animal and/or synthetic origin.

In particular, the waxes have a melting point of greater than 30° C. and better still greater than 45° C.

Apolar Wax

For the purposes of the present invention, the term "apolar wax" means a wax whose solubility parameter at 25° C. as defined below, δa, is equal to 0 $(J/cm^3)^{1/2}$.

The apolar waxes are in particular hydrocarbon-based waxes formed solely from carbon and hydrogen atoms, and free of heteroatoms such as N, O, Si and P.

In particular, the term "apolar wax" means a wax that is formed solely from apolar wax and not a mixture that would also comprise other types of waxes which are not apolar waxes.

As illustrations of apolar waxes that are suitable for use in the invention, mention may be made especially of hydrocarbon-based waxes, for instance microcrystalline waxes, paraffin waxes, ozokerite, polymethylene waxes, polyethylene waxes and microwaxes, especially polyethylene waxes.

Polyethylene waxes that may be mentioned include Performalene 500-L Polyethylene and Performalene 400 Polyethylene sold by New Phase Technologies and Asensa Sc 211 sold by Honeywell.

A polymethylene wax that may be mentioned is Cirebelle 108 sold by Cirebelle.

An ozokerite that may be mentioned is Ozokerite Wax SP 1020 P.

As microcrystalline waxes that may be used, mention may be made of Multiwax W 445® sold by the company Sonneborn, and Microwax HW® and Base Wax 30540® sold by the company Paramelt.

As microwaxes that may be used in the O/O emulsions according to the invention as apolar wax, mention may be made especially of polyethylene microwaxes such as those sold under the names Micropoly 200®, 220®, 220L® and 250S® by the company Micro Powders.

Polar Wax

For the purposes of the present invention, the term "polar wax" means a wax whose solubility parameter at 25° C., δa, is other than 0 $(J/cm^3)^{1/2}$.

In particular, the term "polar wax" means a wax whose chemical structure is formed essentially from, or even constituted of, carbon and hydrogen atoms, and comprising at least one highly electronegative heteroatom such as an oxygen, nitrogen, silicon or phosphorus atom.

The definition and calculation of the solubility parameters in the Hansen three-dimensional solubility space are described in the article by C. M. Hansen: The three-dimensional solubility parameters, J. Paint Technol. 39, 105 (1967).

According to this Hansen space:
  δD characterizes the London dispersion forces derived from the formation of dipoles induced during molecular impacts;
  δp characterizes the Debye interaction forces between permanent dipoles and also the Keesom interaction forces between induced dipoles and permanent dipoles;
  δh characterizes the specific interaction forces (such as hydrogen bonding, acid/base, donor/acceptor, etc.); and
  δa is determined by the equation: $δa=(δp^2+δh^2)^{1/2}$.

The parameters δp, δh, δD and δa are expressed in $(J/cm^3)^{1/2}$.

The polar waxes may in particular be hydrocarbon-based, fluoro or silicone waxes and preferably hydrocarbon-based waxes or silicone waxes.

The term "silicone wax" means an oil comprising at least one silicon atom, especially comprising Si—O groups.

The term "hydrocarbon-based wax" means a wax formed essentially from, or even constituted by, carbon and hydrogen atoms, and optionally oxygen and nitrogen atoms, and that does not contain any silicon or fluorine atoms. It may contain alcohol, ester, ether, carboxylic acid, amine and/or amide groups.

Hydrocarbon-Based Waxes

According to a first preferred embodiment, the polar wax is a hydrocarbon-based wax.

As hydrocarbon-based polar wax, a wax chosen from ester waxes and alcohol waxes is in particular preferred.

According to the invention, the term "ester wax" means a wax comprising at least one ester function. The ester waxes may also be hydroxylated.

According to the invention, the term "alcohol wax" means a wax comprising at least one alcohol function, i.e. comprising at least one free hydroxyl (OH) group.

The following may especially be used as ester wax:
  ester waxes such as those chosen from:
  i) waxes of formula $R_1COOR_2$ in which $R_1$ and $R_2$ represent linear, branched or cyclic aliphatic chains in which the number of atoms ranges from 10 to 50, which may contain a heteroatom such as O, N or P and whose melting point ranges from 25 to 120° C. In particular, an ester wax that may be used is a $C_{20}$-$C_{40}$ alkyl (hydroxystearyloxy) stearate (the alkyl group comprising from 20 to 40 carbon atoms), alone or as a mixture, or a $C_{20}$-$C_{40}$ alkyl stearate.

Such waxes are especially sold under the names Kester Wax K 82 P®, Hydroxypolyester K 82 P®, Kester Wax K 80 P® and Kester Wax K82H by the company Koster Keunen.

Use may also be made of a glycol and butylene glycol montanate (octacosanoate) such as the wax Licowax KPS Flakes (INCI name: glycol montanate) sold by the company Clariant.

ii) bis(1,1,1-trimethylolpropane) tetrastearate, sold under the name Hest 2T-4S® by the company Heterene.

iii) dicarboxylic acid diester waxes of general formula $R_3—(—OCO—R_4—COO—R_5)$, in which $R_3$ and $R_5$ are identical or different, preferably identical and represent a $C_4$-$C_{30}$ alkyl group (alkyl group comprising from 4 to 30 carbon atoms) and $R_4$ represents a linear or branched $C_4$-$C_{30}$ aliphatic group (alkyl group comprising from 4 to 30 carbon atoms) which may or may not contain one or more unsaturated groups. Preferably, the $C_4$-$C_{30}$ aliphatic group is linear and unsaturated.

iv) Mention may also be made of the waxes obtained by catalytic hydrogenation of animal or vegetable oils having linear or branched $C_8$-$C_{32}$ fatty chains, for example such as hydrogenated jojoba oil, hydrogenated sunflower oil, hydrogenated castor oil, hydrogenated coconut oil, and also the waxes obtained by hydrogenation of castor oil esterified with cetyl alcohol, such as those sold under the names Phytowax Ricin 16L64® and 22L73® by the company Sophim. Such waxes are described in patent application FR-A-2 792 190. Mention may be made, as waxes obtained by hydrogenation of olive oil esterified with stearyl alcohol, of those sold under the name Phytowax Olive 18 L 57.

v) Waxes corresponding to the partial or total esters, preferably total esters, of a saturated, optionally hydroxylated $C_{16}$-$C_{30}$ carboxylic acid with glycerol. The term "total esters" means that all the hydroxyl functions of glycerol are esterified.

Examples that may be mentioned include trihydroxystearine (or glyceryl trihydroxystearate), tristearine (or glyceryl tristearate) and tribehenin (or glyceryl tribehenate), alone or as a mixture. Among the suitable compounds, mention may be made of triesters of glycerol and of 12-hydroxystearic acid, or hydrogenated castor oil, for instance Thixcin R and Thixcin E sold by Elementis Specialties.

vi) Mention may also be made of the ester of behenic acid and of glycerol, and in particular mixtures of esters of behenic acid and of glycerol, for instance the glyceryl dibehenate, tribehenin and glyceryl behenate mixture sold by the company Gattefossé under the reference Compritol 888 CG ATO.

vii) Mention may also be made of beeswax, synthetic beeswax, polyglycerolated beeswax, carnauba wax, candelilla wax, oxypropylenated lanolin wax, rice bran wax, ouricury wax, esparto grass wax, cork fibre wax, sugar cane wax, Japan wax, sumac wax, montan wax, orange wax, laurel wax and hydrogenated jojoba wax, and mixtures thereof.

According to another embodiment, the polar wax may be an alcohol wax.

Alcohol waxes that may be mentioned include alcohols, which are preferably linear and preferably saturated, comprising from 16 to 60 carbon atoms, with a melting point of between 25 and 120° C. Examples of alcohol waxes that may be mentioned include the wax Performacol 550-L Alcohol from New Phase Technologies, stearyl alcohol, cetyl alcohol, myristyl alcohol, palmityl alcohol, behenyl alcohol, erucyl alcohol or arachidyl alcohol, or mixtures thereof.

Silicone Waxes

The term "silicone wax" means an oil comprising at least one silicon atom, and in particular comprising Si—O groups.

Among the commercial silicone waxes of this type, mention may be made especially of those sold under the names Abilwax 9810 (Goldschmidt), KF910 and KF7002 (Shin-Etsu), or 176-11481 (General Electric).

The silicone waxes that may be used may also be alkyl or alkoxy dimethicones, and also ($C_{20}$-$C_{60}$)alkyl dimethicones, in particular ($C_{30}$-$C_{45}$)alkyl dimethicones, such as the silicone wax sold under the name SF-1642 by the company GE-Bayer Silicones or C30-45 alkyldimethylsilyl polypropylsilsesquioxane under the name SW-8005® C30 Resin Wax sold by the company Dow Corning.

Mention may also be made of silicone waxes obtained by esterification with a (poly)alkoxylated silicone, such as silicone beeswax, silicone candelilla wax or silicone carnauba wax.

Preferably, the wax(es) are chosen from ester waxes.

Even more preferentially, the wax(es) are chosen from beeswax and a mixture of esters of behenic acid and of glycerol.

Non-Volatile Oils

The solid aggregates may also comprise one or more non-volatile oils.

The term "oil" refers to a non-aqueous, water-immiscible compound, which is liquid at room temperature (25° C.) and atmospheric pressure (760 mmHg).

The term "non-volatile oil" means an oil whose vapour pressure at room temperature and atmospheric pressure is non-zero and less than 0.02 mmHg (2.66 Pa) and better still less than $10^{-3}$ mmHg (0.13 Pa).

Non-volatile oils that may especially be mentioned include:
- hydrocarbon-based oils of animal origin,
- hydrocarbon-based oils of plant origin, synthetic ethers containing from 10 to 40 carbon atoms, such as dicapryl ether,
- synthetic esters, such as the oils of formula $R_1COOR_2$, in which $R_1$ represents a linear or branched fatty acid residue comprising from 1 to 40 carbon atoms and $R_2$ represents a hydrocarbon-based chain, which is in particular branched, containing from 1 to 40 carbon atoms, on condition that $R_1+R_2 \geq 10$. The esters may be chosen especially from fatty acid alcohol esters, for instance cetostearyl octanoate, isopropyl alcohol esters such as isopropyl myristate or isopropyl palmitate, ethyl palmitate, 2-ethylhexyl palmitate, isopropyl stearate, octyl stearate, hydroxylated esters, such as isostearyl lactate or octyl hydroxystearate, alkyl or polyalkyl ricinoleates, hexyl laurate, esters of neopentanoic acid, such as isodecyl neopentanoate or isotridecyl neopentanoate, or esters of isononanoic acid, such as isononyl isononanoate or isotridecyl isononanoate,
- polyol esters and pentaerythritol esters, for instance dipentaerythrityl tetrahydroxystearate/tetraisostearate,
- fatty alcohols that are liquid at room temperature, with a branched and/or unsaturated carbon-based chain containing from 12 to 26 carbon atoms, for instance 2-octyldodecanol, isostearyl alcohol and oleyl alcohol,
- $C_{12}$-$C_{22}$ higher fatty acids, such as oleic acid, linoleic acid, linolenic acid, and mixtures thereof,
- non-phenyl silicone oils, for instance caprylyl methicone, and
- phenyl silicone oils, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates, dimethicones or phenyl trimethicone with a viscosity of less than or equal to 100 cSt, and trimethylpentaphenyltrisiloxane, and mixtures thereof; and also mixtures of these various oils.

Preferably, the aggregates also comprise at least one non-volatile oil, chosen in particular from non-volatile apolar hydrocarbon-based oils and non-volatile ester oils, and mixtures thereof.

For the purposes of the present invention, the term "apolar oil" means an oil whose solubility parameter at 25° C., $\delta_a$, is equal to 0 $(J/cm^3)^{1/2}$.

The definition and calculation of the solubility parameters in the Hansen three-dimensional solubility space are described in the article by C. M. Hansen: The three-dimensional solubility parameters, J. Paint Technol. 39, 105 (1967).

According to this Hansen space:
- $\delta_D$ characterizes the London dispersion forces resulting from the formation of dipoles induced during molecular impacts;
- $\delta_p$ characterizes the Debye interaction forces between permanent dipoles and also the Keesom interaction forces between induced dipoles and permanent dipoles;
- $\delta_h$ characterizes the specific interaction forces (such as hydrogen bonding, acid/base, donor/acceptor interaction forces, etc.); and
- $\delta_a$ is determined by the equation: $\delta a = (\delta p^2 + \delta h^2)^{1/2}$.

The parameters $\delta_p$, $\delta_h$, $\delta_D$ and $\delta_a$ are expressed as $(J/cm^3)$.

Preferably, the non-volatile apolar hydrocarbon-based oil is free of oxygen atoms.

Preferably, the non-volatile apolar hydrocarbon-based oil may be chosen from linear or branched hydrocarbons of mineral or synthetic origin. In particular, it may be chosen from:
- liquid paraffin or derivatives thereof,
- liquid petroleum jelly,
- naphthalene oil,
- polybutylenes, especially Indopol H-100 (molar mass or MW=965 g/mol), Indopol H-300 (MW=1340 g/mol) and Indopol H-1500 (MW=2160 g/mol) sold or manufactured by the company Amoco,
- polyisobutenes and hydrogenated polyisobutenes, especially Parleam® sold by the company Nippon Oil Fats, Panalane H-300 E sold or manufactured by the company Amoco (MW=1340 g/mol), Viseal 20000 sold or manufactured by the company Synteal (MW=6000 g/mol) and Rewopal PIB 1000 sold or manufactured by the company Witco (MW=1000 g/mol),
- decene/butene copolymers and polybutene/polyisobutene copolymers, especially Indopol L-14,
- polydecenes and hydrogenated polydecenes, especially Puresyn 10 (MW=723 g/mol) and Puresyn 150 (MW=9200 g/mol) sold or manufactured by the company Mobil Chemicals,
- and mixtures thereof.

Said non-volatile oil may also be an ester oil, in particular containing between 18 and 70 carbon atoms.

Examples that may be mentioned include monoesters, diesters and triesters.

The ester oils may especially be hydroxylated.

The non-volatile ester oil may preferably be chosen from:
- monoesters comprising between 18 and 40 carbon atoms in total, in particular the monoesters of formula $R_1COOR_2$ in which $R_1$ represents a linear or branched fatty acid residue comprising from 4 to 40 carbon atoms and $R_2$ represents a hydrocarbon-based chain, which is especially branched, containing from 4 to 40 carbon atoms, on condition that $R_1+R_2 \geq 18$, for instance Purcellin oil (cetostearyl octanoate), isononyl isononanoate, $C_{12}$ to $C_{15}$ alkyl benzoates, 2-ethylhexyl palmitate, octyldodecyl neopentanoate, 2-octyldodecyl stearate, 2-octyldodecyl erucate, isostearyl isostearate, 2-octyldodecyl benzoate, alcohol or polyalcohol octanoates, decanoates or ricinoleates, isopropyl myristate, isopropyl palmitate, butyl stearate, hexyl laurate, 2-ethylhexyl palmitate, 2-hexyldecyl laurate, 2-octyldecyl palmitate, 2-octyldodecyl myristate or 2-diethylhexyl succinate. Preferably, they are esters of formula $R_1COOR_2$ in which $R_1$ represents a linear or branched fatty acid residue containing from 4 to 40 carbon atoms and $R_2$ represents a hydrocarbon-based chain that is especially branched, containing from 4 to 40 carbon atoms, $R_1$ and $R_2$ being such that $R_1+R_2 \geq 18$. Preferably, the ester comprises between 18 and 40 carbon atoms in total. Preferred monoesters that may be mentioned include isononyl isononanoate, oleyl erucate and/or 2-octyldodecyl neopentanoate;

diesters, especially comprising between 18 and 60 carbon atoms in total and in particular between 18 and 50 carbon atoms in total. It is especially possible to use diesters of dicarboxylic acids and of monoalcohols, preferably such as diisostearyl malate, or glycol diesters of monocarboxylic acids, such as neopentyl glycol diheptanoate or poly-2-glyceryl diisostearate (especially such as the compound sold under the trade reference Dermol DGDIS by the company Alzo);

triesters, especially comprising between 35 and 70 carbon atoms in total, in particular such as triesters of a tricarboxylic acid, such as triisostearyl citrate, or tridecyl trimellitate, or glycol triesters of monocarboxylic acids such as poly-2-glyceryl triisostearate;

tetraesters, especially with a total carbon number ranging from 35 to 70, such as pentaerythritol or polyglycerol tetraesters of a monocarboxylic acid, for instance pentaerythrityl tetrapelargonate, pentaerythrityl tetraisostearate, pentaerythrityl tetraisononanoate, glyceryl tris(2-decyl)tetradecanoate, poly-2-glyceryl tetraisostearate or pentaerythrityl tetrakis(2-decyl)tetradecanoate;

polyesters obtained by condensation of an unsaturated fatty acid dimer and/or trimer and of diol, such as those described in patent application FR 0 853 634, in particular such as dilinoleic acid and 1,4-butanediol. Mention may especially be made in this respect of the polymer sold by Biosynthis under the name Viscoplast 14436H (INCI name: dilinoleic acid/butanediol copolymer), or copolymers of polyols and of diacid dimers, and esters thereof, such as Hailuscent ISDA;

esters and polyesters of diol dimer and of monocarboxylic or dicarboxylic acid, such as esters of diol dimer and of fatty acid and esters of diol dimer and of dicarboxylic acid dimer, in particular which may be obtained from a dicarboxylic acid dimer derived in particular from the dimerization of an unsaturated fatty acid especially of $C_8$ to $C_{34}$, especially of $C_{12}$ to $C_{22}$, in particular of $C_{16}$ to $C_{20}$ and more particularly of $C_{18}$, such as esters of dilinoleic diacids and of dilinoleic diol dimers, for instance those sold by the company Nippon Fine Chemical under the trade names Lusplan DD-DA5® and DD-DA7®;

vinylpyrrolidone/1-hexadecene copolymers, for instance the product sold under the name Antaron V-216 (also known as Ganex V216) by the company ISP (MW=7300 g/mol), hydrocarbon-based plant oils such as fatty acid triglycerides (which are liquid at room temperature), especially of fatty acids containing from 7 to 40 carbon atoms, such as heptanoic or octanoic acid triglycerides or jojoba oil; mention may be made in particular of saturated triglycerides such as caprylic/capric triglycerides, glyceryl triheptanoate, glyceryl trioctanoate, and $C_{18-36}$ acid triglycerides such as those sold under the reference Dub TGI 24 sold by Stéarineries Dubois; and unsaturated triglycerides such as castor oil, olive oil, ximenia oil and pracaxi oil;

and mixtures thereof.

Preferably, the solid aggregates are formed from 10% to 80% by weight of oil(s) and preferably from 15% to 75% by weight, relative to their total weight.

According to a preferred embodiment, the solid aggregates comprise at least one apolar non-volatile hydrocarbon-based oil and one non-volatile ester oil.

Preferably, the solid aggregates comprise at least two apolar non-volatile hydrocarbon-based oils and one non-volatile ester oil.

According to a particularly preferred embodiment, the solid aggregates comprise cetearyl ethylhexanoate (and) isopropyl myristate, hydrogenated polyisobutene and a mineral oil.

According to a first preferred variant, the solid aggregates comprise cetearyl ethylhexanoate (and) isopropyl myristate, hydrogenated polyisobutene and a mineral oil, and glyceryl dibehenate (and) tribehenin (and) glyceryl behenate.

According to a second preferred variant, the solid aggregates comprise cetearyl ethylhexanoate (and) isopropyl myristate, hydrogenated polyisobutene and a mineral oil, and a beeswax.

Hydrophilic Gelling Agent

For the purposes of the present invention, the term "hydrophilic gelling agent" means a compound that is capable of gelling the aqueous phase of the compositions according to the invention.

The gelling agent is hydrophilic and is thus present in the aqueous phase of the composition.

The gelling agent may be water-soluble or water-dispersible.

As stated above, the aqueous phase of a composition according to the invention is gelled with at least one hydrophilic gelling agent.

The hydrophilic gelling agent may be chosen from synthetic polymeric gelling agents, polymeric gelling agents that are natural or of natural origin, mixed silicates and fumed silicas, and mixtures thereof.

Preferably, the hydrophilic gelling agent may be chosen from synthetic polymeric gelling agents, polymeric gelling agents that are natural or of natural origin, and mixtures thereof.

More preferentially, the hydrophilic gelling agent may be chosen from synthetic polymeric gelling agents.

I. Polymeric Gelling Agents that are Natural or of Natural Origin

The polymeric hydrophilic gelling agents that are suitable for use in the invention may be natural or of natural origin.

For the purposes of the invention, the term "of natural origin" is intended to denote polymeric gelling agents obtained by modification of natural polymeric gelling agents.

These gelling agents may be particulate or non-particulate.

More specifically, these gelling agents fall within the category of polysaccharides.

In general, polysaccharides may be divided into several categories.

Thus, the polysaccharides that are suitable for use in the invention may be homopolysaccharides such as fructans, glucans, galactans and mannans or heteropolysaccharides such as hemicellulose.

Similarly, they may be linear polysaccharides such as pullulan or branched polysaccharides such as gum arabic and amylopectin, or mixed polysaccharides such as starch.

More particularly, the polysaccharides that are suitable for use in the invention may be distinguished according to whether or not they are starchy.

I.A. Starchy Polysaccharides

As representatives of this category, mention may be made most particularly of native starches, modified starches and particulate starches.

Native Starches

The starches that may be used in the present invention are more particularly macromolecules in the form of polymers consisting of elementary moieties which are anhydroglucose units (dextrose), linked via α(1,4) bonds of chemical formula $(C_6H_{10}O_5)_n$. The number of these moieties and their assembly make it possible to distinguish amylose, a molecule formed from about 600 to 1000 linearly linked glucose units, and amylopectin, a polymer branched approximately every 25 glucose residues (α(1,6) bond). The total chain may include between 10 000 and 100 000 glucose residues.

Starch is described in particular in Kirk-Othmer's Encyclopaedia of Chemical Technology, 3rd edition, volume 21, pages 492-507, Wiley Interscience, 1983.

The relative proportions of amylose and of amylopectin, and their degree of polymerization, vary as a function of the botanical origin of the starches. On average, a sample of native starch consists of about 25% amylose and 75% amylopectin.

Occasionally, phytoglycogen is present (between 0% and 20% of the starch), which is an analogue of amylopectin but branched every 10 to 15 glucose residues.

Starch may be in the form of semicrystalline granules: amylopectin is organized in leaflets, amylose forms a less well organized amorphous zone between the various leaflets.

Amylose is organized in a straight helix with six glucoses per turn. It dissociates into assimilable glucose under the action of enzymes, amylases, all the more easily when it is in amylopectin form. Specifically, the helical formation does not promote the accessibility of starch to the enzymes.

Starches are generally in the form of a white powder, which is insoluble in cold water, whose elemental particle size ranges from 3 to 100 microns.

By treating it with hot water, starch paste is obtained. It is exploited in industry for its thickening and gelling properties.

The botanical origin of the starch molecules used in the present invention may be cereals or tubers. Thus, the starches are chosen, for example, from corn starch, rice starch, tapioca starch, cassava starch, barley starch, potato starch, wheat starch, sorghum starch and pea starch.

The native starches are represented, for example, by the products sold under the names C*Amilogel™, Cargill Gel™, C* Gel™, Cargill Gum™, DryGel™ and C*Pharm Gel™ by the company Cargill, under the name Corn Starch by the company Roquette, and under the name Tapioca Pure by the company National Starch.

Modified Starches

The modified starches used in the composition of the invention may be modified via one or more of the following reactions: pregelatinization, degradation (acid hydrolysis, oxidation, dextrinization), substitution (esterification, etherification), crosslinking (esterification), bleaching.

More particularly, these reactions can be carried out in the following way:

pregelatinization by splitting the starch granules (for example drying and cooking in a drying drum);

acid hydrolysis giving rise to very rapid retrogradation on cooling;

oxidation with strong oxidizing agents (alkaline medium, in the presence of sodium hypochlorite NaOCl for example) leading to the depolymerization of the starch molecule and to the introduction of carboxyl groups into the starch molecule (mainly oxidation of the hydroxyl group at $C_6$);

dextrinization in acid medium at high temperature (hydrolysis followed by repolymerization);

crosslinking with functional agents capable of reacting with the hydroxyl groups of the starch molecules, which will thus bond together (for example with glyceryl and/or phosphate groups);

esterification in alkaline medium for the grafting of functional groups, especially C1-C6 acyl (acetyl), C1-C6 hydroxyalkyl (hydroxyethyl or hydroxypropyl), carboxymethyl or octenylsuccinic.

Monostarch phosphates (of the type St-O—PO—(OX)2), distarch phosphates (of the type St-O—PO—(OX)—O-St) or even tristarch phosphates (of the type St-O—PO—(O-St)2) or mixtures thereof may especially be obtained by crosslinking with phosphorus compounds.

X especially denotes alkali metals (for example sodium or potassium), alkaline-earth metals (for example calcium or magnesium), ammonium salts, amine salts, for instance those of monoethanolamine, diethanolamine, triethanolamine, 3-amino-1,2-propanediol, or ammonium salts derived from basic amino acids such as lysine, arginine, sarcosine, ornithine or citrulline.

The phosphorus compounds can, for example, be sodium tripolyphosphate, sodium orthophosphate, phosphorus oxychloride or sodium trimetaphosphate.

According to the invention, it is also possible to use amphoteric starches, these amphoteric starches containing one or more anionic groups and one or more cationic groups. The anionic and cationic groups may be linked to the same reactive site of the starch molecule or to different reactive sites; they are preferably linked to the same reactive site. The anionic groups may be of carboxylic, phosphate or sulfate type, preferably carboxylic. The cationic groups can be of primary, secondary, tertiary or quaternary amine type.

The amphoteric starches are in particular chosen from the compounds having the following formulae:

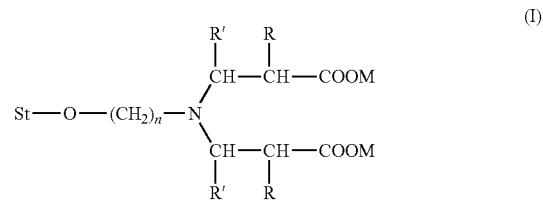

(I)

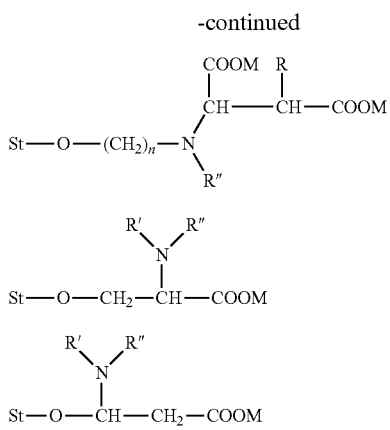

in which:
St—O represents a starch molecule;
R, which may be identical or different, represents a hydrogen atom or a methyl radical;
R', which may be identical or different, represents a hydrogen atom, a methyl radical or a —COOH group;
n is an integer equal to 2 or 3;
M, which may be identical or different, denotes a hydrogen atom, an alkali metal or alkaline-earth metal such as Na, K, Li or $NH_4$, a quaternary ammonium or an organic amine;
R" represents a hydrogen atom or an alkyl radical containing from 1 to 18 carbon atoms.

These compounds are especially described in U.S. Pat. Nos. 5,455,340 and 4,017,460.

The starch molecules may be derived from any plant source of starch, especially such as corn, potato, oat, rice, tapioca, sorghum, barley or wheat. It is also possible to use the hydrolysates of the starches mentioned above.

The modified starches are represented, for example, by the products sold under the names C*Tex-Instant (pregelatinized adipate), C*StabiTex-Instant (pregelatinized phosphate), C*PolarTex-Instant (pregelatinized hydroxypropyl), C*Set (acid hydrolysis, oxidation), C*size (oxidation), C*BatterCrisp (oxidation), C*DrySet (dextrinization), C*Tex™ (acetyl distarch adipate), C*PolarTex™ (hydroxypropyl distarch phosphate), C* StabiTex™ (distarch phosphate, acetyl distarch phosphate) by the company Cargill, by distarch phosphates or compounds rich in distarch phosphate such as the product sold under the references Prejel VA-70-T AGGL (gelatinized hydroxypropyl cassava distarch phosphate) or Prejel TK1 (gelatinized cassava distarch phosphate) or Prejel 200 (gelatinized acetyl cassava distarch phosphate) by the company Avebe or Structure Zea from National Starch (gelatinized corn distarch phosphate).

As examples of oxidized starches, use will be made especially of those sold under the name C*size from the company Cargill.

The native or modified starches described above may be advantageously used in a proportion of from 0.1% to 8% by weight of solids and preferably at about 1% by weight, relative to the total weight of the aqueous phase.

Particulate Starches

Particulate starches that may be mentioned in particular include:
starches grafted with an acrylic polymer (homopolymer or copolymer) and especially with sodium polyacrylate, for instance those sold under the names Sanfresh ST100MC by the company Sanyo Chemical Industries or Makimousse 25, Makimousse 12 by the company Daito Kasei (INCI name: Sodium polyacrylate starch), hydrolyzed starches grafted with an acrylic polymer (homopolymer or copolymer), and especially acryloacrylamide/sodium acrylate copolymer, for instance those sold under the names Water Lock A-240, A-180, B-204, D-223, A-100, C-200 and D-223 by the company Grain Processing (INCI name: Starch/acrylamide/sodium acrylate copolymer);
polymers based on starch, gum and cellulose derivative, such as the product containing starch and sodium carboxymethylcellulose, for instance the product sold under the name Lysorb 220 by the company Lysac.

Mention may be made most particularly of $C_1$-$C_4$ carboxyalkyl starches, also referred to hereinbelow as "carboxyalkyl starch". These compounds are obtained by grafting carboxyalkyl groups onto one or more alcohol functions of starch, especially by reaction of starch and of sodium monochloroacetate in alkaline medium.

The carboxyalkyl groups are generally attached via an ether function, more particularly to carbon 1. The degree of substitution with carboxyalkyl units of the $C_1$-$C_4$ carboxyalkyl starch preferably ranges from 0.1 to 1 and more particularly from 0.15 to 0.5. The degree of substitution is defined according to the present invention as being the mean number of hydroxyl groups substituted with an ester or ether group per monosaccharide unit of the polysaccharide.

The carboxyalkyl starches are advantageously used in the form of salts and especially of salts of alkali metals or alkaline-earth metals such as Na, K, Li, $NH_4$, or salts of a quaternary ammonium or of an organic amine such as monoethanolamine, diethanolamine or triethanolamine. The (C1-C4) carboxyalkyl starches are advantageously, in the context of the present invention, carboxymethyl starches. The carboxymethyl starches preferably comprise units having the following formula:

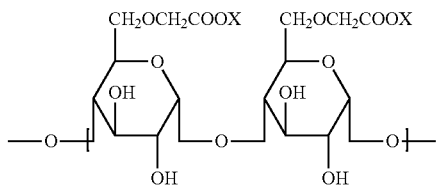

in which X, optionally covalently bonded to the carboxylic unit, denotes a hydrogen atom, an alkali metal or alkaline-earth metal such as Na, K, Li, $NH_4$, a quaternary ammonium or an organic amine, for instance monoethanolamine, diethanolamine or triethanolamine.

Preferably, X denotes a cation $Na^+$. The carboxyalkyl starches that may be used according to the present invention are preferably non-pregelatinized carboxyalkyl starches. The carboxyalkyl starches that may be used according to the present invention are preferably partially or totally crosslinked carboxyalkyl starches.

In general, a crosslinked carboxyalkyl starch has, in contrast with a non-crosslinked carboxyalkyl starch, an increased, controllable viscosity of increased stability. The crosslinking thus makes it possible to reduce the syneresis phenomena and to increase the resistance of the gel to shear effects.

The carboxyalkyl starches under consideration according to the invention are more particularly potato carboxyalkyl starches. Thus, the carboxyalkyl starches that may be used according to the present invention are preferably sodium salts of carboxyalkyl starches, in particular a sodium salt of potato carboxymethyl starch, sold especially under the name Primojel® by the company DMV International or Glycolys® and Glycolys® LV by the company Roquette.

According to a particular mode, use will be made of the potato carboxymethyl starches sold especially under the name Glycolys® by the company Roquette. As stated previously, the $C_1$-$C_4$ carboxyalkyl starch particles are present in the compositions according to the invention in a swollen and non-split form. This swelling may be characterized by a swelling power Q which may advantageously be between 10 and 30 ml/g and preferably between 15 and 25 ml (volume of adsorbed liquid)/g of dry particulate material.

Thus, the size of the swollen carboxyalkyl starch particles used according to the present invention generally ranges from 25 to 300 µm. For example, the gel Primojel® containing 10% by weight of potato carboxyalkyl starch and sodium salt in water contains more than 80% of swollen particles of this starch with a diameter of greater than 50 microns and more particularly greater than 100 microns.

According to a preferred embodiment variant of the invention, these particles are used for the preparation of the compositions according to the invention, in this swollen particulate state. To do so, these particles are advantageously used in the form of an aqueous gel either prepared beforehand or already commercially available. The gels under consideration according to the invention are advantageously translucent.

For example, a carboxymethyl starch gel such as Primojel® which is at a concentration of 10% by weight may be adjusted to the required concentration before being used for preparing the expected composition.

Such a particulate starch may be used in a proportion of from 0.1% to 5% by weight of solids relative to the total weight of the aqueous phase, preferably between 0.5% and 2.5% by weight and in particular in a proportion of about 1.5% by weight, relative to the total weight of the aqueous phase.

According to one embodiment variant, the hydrophilic gelling agent is non-starchy.

I.B. Non-Starchy Polysaccharides

In general, the non-starchy polysaccharides may be chosen from polysaccharides produced by microorganisms; polysaccharides isolated from algae, and higher plant polysaccharides, such as homogeneous polysaccharides, in particular celluloses and derivatives thereof or fructosans, heterogeneous polysaccharides such as gum arabics, galactomannans, glucomannans and pectins, and derivatives thereof; and mixtures thereof.

In particular, the polysaccharides may be chosen from fructans, gellans, glucans, amylose, amylopectin, glycogen, pullulan, dextrans, celluloses and derivatives thereof, in particular methylcelluloses, hydroxyalkylcelluloses, ethylhydroxyethylcelluloses and carboxymethylcelluloses, mannans, xylans, lignins, arabans, galactans, galacturonans, alginate-based compounds, chitin, chitosans, glucuronoxylans, arabinoxylans, xyloglucans, glucomannans, pectic acids and pectins, arabinogalactans, carrageenans, agars, glycosaminoglucans, gum arabics, tragacanth gums, ghatti gums, karaya gums, locust bean gums, galactomannans such as guar gums and nonionic derivatives thereof, in particular hydroxypropyl guar, and ionic derivatives thereof, biopolysaccharide gums of microbial origin, in particular scleroglucan or xanthan gums, mucopolysaccharides, and in particular chondroitin sulfates, and mixtures thereof.

These polysaccharides may be chemically modified, especially with urea or urethane groups or by hydrolysis, oxidation, esterification, etherification, sulfation, phosphatation, amination, amidation or alkylation reaction, or by several of these modifications.

The derivatives obtained may be anionic, cationic, amphoteric or nonionic.

Advantageously, the polysaccharides may be chosen from carrageenans, in particular kappa carrageenan, gellan gum, agar-agar, xanthan gum, alginate-based compounds, in particular sodium alginate, scleroglucan gum, guar gum, inulin and pullulan, and mixtures thereof.

Preferably, the polysaccharide may be xanthan gum.

In general, the compounds of this type that may be used in the present invention are chosen from those described especially in Kirk-Othmer's Encyclopedia of Chemical Technology, Third Edition, 1982, volume 3, pp. 896-900, and volume 15, pp. 439-458, in Polymers in Nature by E. A. MacGregor and C. T. Greenwood, published by John Wiley & Sons, Chapter 6, pp. 240-328, 1980, in the book by Robert L. Davidson entitled Handbook of Water-Soluble Gums and Resins published by McGraw Hill Book Company (1980) and in Industrial Gums—Polysaccharides and their Derivatives, edited by Roy L. Whistler, Second Edition, published by Academic Press Inc.

Such a gelling agent may be used in a proportion of from 0.1% to 8% by weight of solids relative to the total weight of the aqueous phase, especially from 0.1% to 6% by weight, preferably between 0.5% and 2.5% by weight and in particular in a proportion of about 1%, or alternatively in a proportion of about 1.5% by weight, relative to the total weight of the aqueous phase.

More precisely, these polysaccharides that are suitable for use in the invention may be distinguished according to whether they are derived from microorganisms, from algae or from higher plants, and are detailed below.

Polysaccharides Produced by Microorganisms

Xanthan

Xanthan is a heteropolysaccharide produced on an industrial scale by the aerobic fermentation of the bacterium *Xanthomonas campestris*. Its structure consists of a main chain of β(1,4)-linked β-D-glucoses, similar to cellulose. One glucose molecule in two bears a trisaccharide side chain composed of an α-D-mannose, a β-D-glucuronic acid and a terminal β-D-mannose. The internal mannose residue is generally acetylated on carbon 6. About 30% of the terminal mannose residues bear a pyruvate group linked in chelated form between carbons 4 and 6. The charged pyruvic acids and glucuronic acids are ionizable, and are thus responsible for the anionic nature of xanthan (negative charge down to a pH equal to 1). The content of pyruvate and acetate residues varies according to the bacterial strain, the fermentation process, the conditions after fermentation and the purification steps. These groups may be neutralized in commercial products with $Na^+$, $K^+$ or $Ca^{2+}$ ions (Satia company, 1986). The neutralized form may be converted into the acid form by ion exchange or by dialysis of an acidic solution.

Xanthan gums have a molecular weight of between 1 000 000 and 50 000 000 and a viscosity of between 0.6 and 1.65 Pa·s for an aqueous composition containing 1% of xanthan gum (measured at 25° C. on a Brookfield viscometer of LVT type at 60 rpm).

Xanthan gums are represented, for example, by the products sold under the names Rhodicare by the company Rhodia Chimie, under the name Satiaxane™ by the company Cargill Texturizing Solutions (for the food, cosmetic and pharmaceutical industries), under the name Novaxan™ by the company ADM, and under the names Kelzan® and Keltrol® by the company CP-Kelco.

Advantageously, a composition according to the invention comprises a xanthan gum.

The xanthan gum(s) may be used in a proportion of from 0.01% to 5% by weight of solids relative to the total weight of the composition, especially from 0.05% to 2% by weight, preferably between 0.05% and 1% by weight, in particular between 0.1% and 0.2% by weight, relative to the total weight of the composition.

Pullulan

Pullulan is a polysaccharide consisting of maltotriose units, known under the name $\alpha(1,4)$-$\alpha(1,6)$-glucan. Three glucose units in maltotriose are connected via an $\alpha(1,4)$ glycoside bond, whereas the consecutive maltotriose units are connected to each other via an $\alpha(1,6)$ glycoside bond.

Pullulan is produced, for example, under the reference Pullulan PF 20 by the group Hayashibara in Japan.

Dextran and Dextran Sulfate

Dextran is a neutral polysaccharide not bearing any charged groups, which is biologically inert, prepared by fermentation of beet sugar containing solely hydroxyl groups.

It is possible to obtain dextran fractions of different molecular weights from native dextran by hydrolysis and purification. Dextran may in particular be in the form of dextran sulfate.

Dextran is represented, for example, by the products sold under the name Dextran or Dextran T by the company Pharmacosmos, or under the name Dextran 40 Powder or Dextran 70 Powder by the company Meito Sangyo Co. Dextran sulfate is sold by the company PK Chemical A/S under the name Dextran sulphate.

Succinoglycan

Succinoglycan is an extracellular polymer of high molecular weight produced by bacterial fermentation, consisting of octasaccharide repeating units (repetition of 8 sugars). Succinoglycans are sold, for example, under the name Rheozan by the company Rhodia.

Scleroglucan

Scleroglucan is a nonionic branched homopolysaccharide consisting of $\beta$-D-glucan units. The molecules consist of a linear main chain formed from D-glucose units linked via $\beta(1,3)$ bonds and of which one in three is linked to a side D-glucose unit via a $\beta(1,6)$ bond.

A more complete description of scleroglucans and of their preparation may be found in patent U.S. Pat. No. 3,301,848.

Scleroglucan is sold, for example, under the name Amigel by the company Alban Muller, or under the name Actigum™ CS by the company Cargill.

Gellan Gum

Gellan gum is an anionic linear heteropolyoside based on oligoside units composed of 4 saccharides (tetra-oside). D-Glucose, L-rhamnose and D-glucuronic acid in 2:1:1 proportions are present in gellan gum in the form of monomer elements.

It is sold, for example, under the name Kelcogel CG LA by the company CP Kelco.

Polysaccharides Isolated from Algae

Galactans

The polysaccharide according to the invention may be a galactan chosen especially from agar and carrageenans.

Carrageenans are anionic polysaccharides constituting the cell walls of various red algae (Rhodophyceae) belonging to the Gigartinacae, Hypneaceae, Furcellariaceae and Polyideaceae families. They are generally obtained by hot aqueous extraction from natural strains of said algae. These linear polymers, formed by disaccharide units, are composed of two D-galactopyranose units linked alternately by $\alpha(1,3)$ and $\beta(1,4)$ bonds. They are highly sulfated polysaccharides (20-50%) and the $\alpha$-D-galactopyranosyl residues may be in 3,6-anhydro form. Depending on the number and position of sulfate-ester groups on the repeating disaccharide of the molecule, several types of carrageenans are distinguished, namely: kappa-carrageenans, which bear one sulfate-ester group, iota-carrageenans, which bear two sulfate-ester groups, and lambda-carrageenans, which bear three sulfate-ester groups.

Carrageenans are composed essentially of potassium, sodium, magnesium, triethanolamine and/or calcium salts of polysaccharide sulfate esters.

Carrageenans are sold especially by the company SEPPIC under the name Solagum®, by the company Gelymar under the names Carragel®, Carralact® and Carrasol®, by the company Cargill, under the names Satiagel™ and Satiagum™, and by the company CP-Kelco under the names Genulacta®, Genugel® and Genuvisco®.

Galactans of agar type are galactose polysaccharides contained in the cell wall of some of these species of red algae (rhodophyceae). They are formed from a polymer group whose base backbone is a $\beta(1,3)$ D-galactopyranose and $\alpha(1,4)$ L 3-6 anhydrogalactose chain, these units repeating regularly and alternately. The differences within the agar family are due to the presence or absence of solvated methyl or carboxyethyl groups. These hybrid structures are generally present in variable percentage, depending on the species of algae and the harvest season.

Agar-agar is a mixture of polysaccharides (agarose and agaropectin) of high molecular mass, between 40 000 and 300 000 g·mol-1. It is obtained by manufacturing algal extraction liquors, generally by autoclaving, and by treating these liquors which comprise about 2% of agar-agar, so as to extract the latter.

Agar is produced, for example, by the group B&V Agar Producers under the names Gold Agar, Agarite and Grand Agar by the company Hispanagar, and under the names Agar-Agar, QSA (Quick Soluble Agar), and Puragar by the company Setexam.

Furcellaran

Furcellaran is obtained commercially from red algae *Furcellaria fasztigiata*. Furcellaran is produced, for example, by the company Est-Agar.

Alginate-Based Compound

For the purposes of the invention, the term "alginate-based compound" means alginic acid, alginic acid derivatives and salts of alginic acid (alginates) or of said derivatives.

Preferably, the alginate-based compound is water-soluble.

Alginic acid, a natural substance resulting from brown algae or certain bacteria, is a polyuronic acid composed of 2 uronic acids linked by 1,4-glycosidic bonds: $\beta$-D-mannuronic (M) acid and $\alpha$-L-glucuronic (G) acid.

Alginic acid is capable of forming water-soluble salts (alginates) with alkali metals such as sodium, potassium or lithium, substituted cations of lower amines and of ammonium such as methylamine, ethanolamine, diethanolamine or triethanolamine. These alginates are water-soluble in aqueous medium at a pH equal to 4, but dissociate into alginic acid at a pH below 4.

This (these) alginate-based compound(s) are capable of crosslinking in the presence of at least one crosslinking agent, by formation of ionic bonds between said alginate-based compound(s) and said crosslinking agent(s). The formation of multiple crosslinking between several molecules of said alginate-based compound(s) leads to the formation of a water-insoluble gel.

Use is preferably made of alginate-based compounds that have a weight-average molecular mass ranging from 10 000 to 1 000 000, preferably from 15 000 to 500 000 and better still from 20 000 to 250 000.

According to a preferred embodiment, the alginate-based compound is alginic acid and/or a salt thereof.

Advantageously, the alginate-based compound is an alginate salt, and preferably sodium alginate.

The alginate-based compound may be chemically modified, especially with urea or urethane groups or by hydrolysis, oxidation, esterification, etherification, sulfatation, phosphatation, amination, amidation or alkylation reaction, or by several of these modifications.

The derivatives obtained may be anionic, cationic, amphoteric or nonionic.

The alginate-based compounds that are suitable for use in the invention may be represented, for example, by the products sold under the names Kelcosol, Satialgine™, Cecalgum™ or Algogel™ by the company Cargill Products, under the name Protanal™ by the company FMC Biopolymer, under the name Grindsted® Alginate by the company Danisco, under the name Kimica Algin by the company Kimica, and under the names Manucol® and Manugel® by the company ISP.

Polysaccharides of Higher Plants

This category of polysaccharides may be divided into homogeneous polysaccharides (only one saccharide species) and heterogeneous polysaccharides composed of several types of saccharides.

a) Homogeneous Polysaccharides and Derivatives Thereof

The polysaccharide according to the invention may be chosen from celluloses and derivatives or fructosans.

Cellulose and Derivatives

The polysaccharide according to the invention may also be a cellulose or a derivative thereof, especially cellulose ethers or esters (e.g.: methylcellulose, carboxymethylcellulose, hydroxymethylcellulose, hydroxyethylcellulose, hydroxypropylcellulose, hydroxymethylpropylcellulose, cellulose acetate, cellulose nitrate, nitrocellulose).

The invention may also contain a cellulose-based associative polymer. According to the invention, the term "cellulose-based compound" means any polysaccharide compound bearing in its structure linear sequences of anhydroglucopyranose residues (AGU) linked together via $\beta(1,4)$ bonds. The repeating unit is the cellobiose dimer. The AGUs are in chair conformation and bear 3 hydroxyl functions: 2 secondary alcohols (in position 2 and 3) and a primary alcohol (in position 6). The polymers thus formed combine together via intermolecular bonds of hydrogen bond type, thus giving the cellulose a fibrillar structure (about 1500 molecules per fibre).

The degree of polymerization differs enormously depending on the origin of the cellulose; its value may range from a few hundred to several tens of thousands.

Cellulose has the following chemical formula:

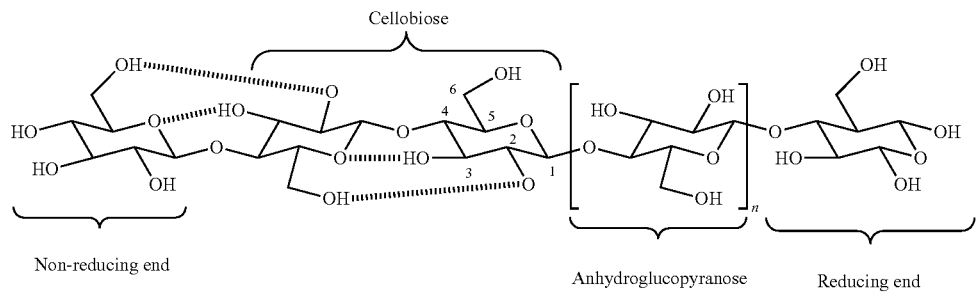

The hydroxyl groups of cellulose may react partially or totally with various chemical reagents to give cellulose derivatives having intrinsic properties. The cellulose derivatives may be anionic, cationic, amphoteric or nonionic. Among these derivatives, cellulose ethers, cellulose esters and cellulose ester ethers are distinguished.

Among the nonionic cellulose ethers, mention may be made of alkylcelluloses such as methylcelluloses and ethylcelluloses; hydroxyalkylcelluloses such as hydroxymethylcelluloses, hydroxyethylcelluloses and hydroxypropylcelluloses; and mixed hydroxy-alkylalkylcelluloses such as hydroxypropylmethylcelluloses, hydroxyethylmethylcelluloses, hydroxyethylethylcelluloses and hydroxybutylmethylcelluloses.

Among the anionic cellulose ethers, mention may be made of carboxyalkyl celluloses and salts thereof. By way of example, mention may be made of carboxymethylcelluloses, carboxymethylmethylcelluloses and carboxymethylhydroxyethylcelluloses and sodium salts thereof.

Among the cationic cellulose ethers, mention may be made of crosslinked or non-crosslinked, quaternized hydroxyethylcelluloses.

The quaternizing agent may in particular be glycidyltrimethylammonium chloride or a fatty amine such as laurylamine or stearylamine. Another cationic cellulose ether that may be mentioned is hydroxyethylcellulosehydroxypropyltrimethylammonium.

The quaternized cellulose derivatives are, in particular:
quaternized celluloses modified with groups comprising at least one fatty chain, such as alkyl, arylalkyl or alkylaryl groups comprising at least 8 carbon atoms, or mixtures thereof,
quaternized hydroxyethylcelluloses modified with groups comprising at least one fatty chain, such as alkyl, arylalkyl or alkylaryl groups comprising at least 8 carbon atoms, or mixtures thereof.

The alkyl radicals borne by the above quaternized celluloses or hydroxyethylcelluloses preferably contain from 8 to 30 carbon atoms. The aryl radicals preferably denote phenyl, benzyl, naphthyl or anthryl groups.

Examples of quaternized alkylhydroxyethylcelluloses containing $C_8$-$C_{30}$ fatty chains that may be indicated include the products Quatrisoft LM 200, Quatrisoft LM-X 529-18-A, Quatrisoft LM-X 529-18B ($C_{12}$ alkyl) and Quatrisoft LM-X 529-8 ($C_{18}$ alkyl) sold by the company Amerchol and the products Crodacel QM, Crodacel QL ($C_{12}$ alkyl) and Crodacel QS ($C_{18}$ alkyl) sold by the company Croda.

Among the cellulose derivatives, mention may also be made of:
celluloses modified with groups comprising at least one fatty chain, for instance hydroxyethylcelluloses modified with groups comprising at least one fatty chain, such as alkyl groups, especially of $C_8$-$C_{22}$, arylalkyl and alkylaryl groups, such as Natrosol Plus Grade 330 CS (C16 alkyls) sold by the company Aqualon, and
celluloses modified with polyalkylene glycol alkylphenyl ether groups, such as the product Amercell Polymer HM-1500 (nonylphenyl polyethylene glycol (15) ether) sold by the company Amerchol.

Among the cellulose esters are mineral esters of cellulose (cellulose nitrates, sulfates, phosphates, etc.), organic cellulose esters (cellulose monoacetates, triacetates, amidopropionates, acetatebutyrates, acetatepropionates and acetatetrimellitates, etc.), and mixed organic/mineral esters of cellulose, such as cellulose acetatebutyrate sulfates and cellulose acetatepropionate sulfates. Among the cellulose ester ethers, mention may be made of hydroxypropylmethylcellulose phthalates and ethylcellulose sulfates.

The cellulose-based compounds of the invention may be chosen from unsubstituted celluloses and substituted celluloses.

The celluloses and derivatives are represented, for example, by the products sold under the names Avicel® (microcrystalline cellulose, MCC) by the company FMC Biopolymers, under the name Cekol (carboxymethylcellulose) by the company Noviant (CP-Kelco), under the name Akucell AF (sodium carboxymethylcellulose) by the company Akzo Nobel, under the name Methocel™ (cellulose ethers) and Ethocel™ (ethylcellulose) by the company Dow, and under the names Aqualon® (carboxymethylcellulose and sodium carboxymethylcellulose), Benecel® (methylcellulose), Blanose™ (carboxymethylcellulose), Culminal® (methylcellulose, hydroxypropylmethylcellulose), Klucel® (hydroxypropylcellulose), Polysurf® (cetylhydroxyethylcellulose) and Natrosol® CS (hydroxyethylcellulose) by the company Hercules Aqualon.

Fructosans

The polysaccharide according to the invention may especially be a fructosan chosen from inulin and derivatives thereof (especially dicarboxy and carboxymethyl inulins).

Fructans or fructosans are oligosaccharides or polysaccharides comprising a sequence of anhydrofructose units optionally combined with several saccharide residues other than fructose. Fructans may be linear or branched. Fructans may be products obtained directly from a plant or microbial source or alternatively products whose chain length has been modified (increased or decreased) by fractionation, synthesis or hydrolysis, in particular enzymatic. Fructans generally have a degree of polymerization from 2 to about 1000 and preferably from 2 to about 60.

Three groups of fructans are distinguished. The first group corresponds to products whose fructose units are for the most part linked via $\beta(2,1)$ bonds. These are essentially linear fructans such as inulins.

The second group also corresponds to linear fructoses, but the fructose units are essentially linked via $\beta(2,6)$ bonds. These products are levans.

The third group corresponds to mixed fructans, i.e. containing $\beta(2,6)$ and $\beta(2,1)$ sequences. These are essentially branched fructans, such as graminans.

The preferred fructans in the compositions according to the invention are inulins. Inulin may be obtained, for example, from chicory, dahlia or Jerusalem artichoke, preferably from chicory.

In particular, the polysaccharide, especially the inulin, has a degree of polymerization from 2 to about 1000 and preferably from 2 to about 60, and a degree of substitution of less than 2 on the basis of one fructose unit.

The inulin used for this invention is represented, for example, by the products sold under the name Beneo™ inulin by the company Orafti, and under the name Frutafit® by the company Sensus.

b) Heterogeneous Polysaccharides and Derivatives Thereof

The polysaccharides that may be used according to the invention may be gums, for instance cassia gum, karaya gum, konjac gum, gum tragacanth, tara gum, acacia gum or gum arabic.

Gum Arabic

Gum arabic is a highly branched acidic polysaccharide which is in the form of mixtures of potassium, magnesium and calcium salts. The monomer elements of the free acid (arabic acid) are D-galactose, L-arabinose, L-rhamnose and D-glucuronic acid.

Galactomannans (guar, locust bean, fenugreek, tara gum) and derivatives (guar phosphate, hydroxypropyl guar, etc.)

Galactomannans are nonionic polyosides extracted from the endosperm of leguminous seeds, of which they constitute the storage carbohydrate.

Galactomannans are macromolecules consisting of a main chain of $\beta(1,4)$ linked D-mannopyranose units, bearing side branches consisting of a single D-galactopyranose unit $\alpha(1,6)$ linked to the main chain. The various galactomannans differ, firstly, by the proportion of α-D-galactopyranose units present in the polymer, and secondly by significant differences in terms of distribution of galactose units along the mannose chain.

The mannose/galactose (M/G) ratio is about 2 for guar gum, 3 for tara gum and 4 for locust bean gum.

Galactomannans have the following chemical structure:

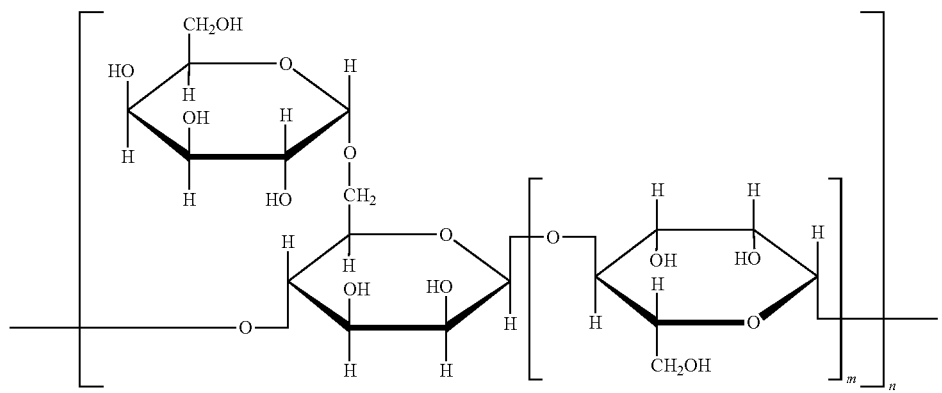

m = 3: Locust beam gum
m = 1: Guar gum
m = 2: Tara gum

Guar

Guar gum is characterized by a mannose/galactose ratio of the order of 2/1. The galactose group is regularly distributed along the mannose chain.

The guar gums that may be used according to the invention may be nonionic, cationic or anionic. According to the invention, use may be made of chemically modified or unmodified nonionic guar gums.

The unmodified nonionic guar gums are, for example, the products sold under the names Vidogum GH, Vidogum G and Vidocrem by the company Unipektin and under the name Jaguar by the company Rhodia, under the name Meypro® Guar by the company Danisco, under the name Viscogum™ by the company Cargill, and under the name Supercol® guar gum by the company Aqualon.

The hydrolysed nonionic guar gums that may be used according to the invention are represented, for example, by the products sold under the name Meyprodor® by the company Danisco.

The modified nonionic guar gums that may be used according to the invention are preferably modified with $C_1$-$C_6$ hydroxyalkyl groups, among which mention may be made, for example, of hydroxymethyl, hydroxyethyl, hydroxypropyl and hydroxybutyl groups.

Such nonionic guar gums optionally modified with hydroxyalkyl groups are sold, for example, under the trade names Jaguar HP60, Jaguar HP 105 and Jaguar HP 120 (hydroxypropyl guar) by the company Rhodia or under the name N-Hance® HP (hydroxypropyl guar) by the company Aqualon.

The cationic galactomannan gums preferably have a cationic charge density of less than or equal to 1.5 meq/g, more particularly between 0.1 and 1 meq/g. The charge density may be determined by the Kjeldahl method. It generally corresponds to a pH of the order of 3 to 9.

In general, for the purposes of the present invention, the term "cationic galactomannan gum" means any galactomannan gum containing cationic groups and/or groups that can be ionized into cationic groups.

The preferred cationic groups are chosen from those comprising primary, secondary, tertiary and/or quaternary amine groups.

The cationic galactomannan gums used generally have a weight-average molecular mass of between 500 and $5 \times 10^6$ approximately and preferably between $10^3$ and $3 \times 10^6$ approximately.

The cationic galactomannan gums that may be used according to the present invention are, for example, gums comprising tri($C_1$-$C_4$)alkylammonium cationic groups. Preferably, 2% to 30% by number of the hydroxyl functions of these guar gums bear trialkylammonium cationic groups.

Mention may very particularly be made, among these trialkylammonium groups, of the trimethylammonium and triethylammonium groups.

Even more preferentially, these groups represent from 5% to 20% by weight relative to the total weight of the modified galactomannan gum.

According to the invention, the cationic galactomannan gum is preferably a guar gum comprising hydroxypropyltrimethylammonium groups, i.e. a guar gum modified, for example, with 2,3-epoxypropyltrimethylammonium chloride.

These galactomannan gums, in particular guar gums modified with cationic groups are products already known per se and are, for example, described in U.S. Pat. Nos. 3,589,578 and 4,031,307. Such products are moreover sold especially under the trade names Jaguar EXCEL, Jaguar C13 S, Jaguar C 15, Jaguar C 17 and Jaguar C162 (Guar Hydroxypropyltrimonium Chloride) by the company Rhodia, under the name Amilan® Guar (Guar Hydroxypropyltrimonium Chloride) by the company Degussa, and under the name N-Hance® 3000 (Guar Hydroxypropyltrimonium Chloride) by the company Aqualon.

The anionic guar gums that may be used according to the invention are polymers comprising groups derived from carboxylic, sulfonic, sulfenic, phosphoric, phosphonic or pyruvic acid. The anionic group is preferably a carboxylic acid group. The anionic group may also be in the form of an acid salt, especially a sodium, calcium, lithium or potassium salt.

The anionic guar gums that may be used according to the invention are preferentially carboxymethyl guar derivatives (carboxymethyl guar or carboxymethyl hydroxypropyl guar).

Locust Bean

Locust bean gum is extracted from the seeds of the locust bean tree (Ceratonia siliqua).

The unmodified locust bean gum that may be used in this invention is sold, for example, under the name Viscogum™ by the company Cargill, under the name Vidogum L by the company Unipektin and under the name Grinsted® LBG by the company Danisco.

The chemically modified locust bean gums that may be used in this invention may be represented, for example, by the cationic locust beans sold under the name Catinal CLB (locust bean hydroxypropyltrimonium chloride) by the company Toho.

Tara Gum

The tara gum that may be used in the context of this invention is sold, for example, under the name Vidogum SP by the company Unipektin.

Glucomannans (Konjac Gum)

Glucomannan is a polysaccharide of high molecular weight (500 000<Mglucomannan<2 000 000) composed of D-mannose and D-glucose units with a branch every 50 or 60 units approximately. It is found in wood, but is also the main constituent of konjac gum. Konjac (Amorphophallus konjac) is a plant of the Araceae family.

The products that may be used according to the invention are sold, for example, under the names Propol® and Rheolex® by the company Shimizu.

LM and HM Pectins, and Derivatives

Pectins are linear polymers of α-D-galacturonic acid (at least 65%) linked in positions 1 and 4 with a certain proportion of carboxylic groups esterified with a methanol group. About 20% of the sugars constituting the pectin molecule are neutral sugars (L-rhamnose, D-glucose, D-galactose, L-arabinose, D-xylose). L-Rhamnose residues are found in all pectins, incorporated into the main chain in positions 1,2.

Uronic acid molecules bear carboxyl functions. This function gives pectins the capacity for exchanging ions, when they are in COO⁻ form. Divalent ions (in particular calcium) have the capacity of forming ionic bridges between two carboxyl groups of two different pectin molecules.

In the natural state, a certain proportion of the carboxylic groups are esterified with a methanol group. The natural degree of esterification of a pectin may range between 70% (apple, lemon) and 10% (strawberry) depending on the source used. Using pectins with a high degree of esterification, it is possible to hydrolyse the —COOCH$_3$ groups so as to obtain weakly esterified pectins. Depending on the proportion of methylated or non-methylated monomers, the chain is thus more or less acidic. HM (high-methoxy) pectins are thus defined as having a degree of esterification of greater than 50%, and LM (low-methoxy) pectins are defined as having a degree of esterification of less than 50%.

In the case of amidated pectins, the —OCH$_3$ group is substituted with an —NH$_2$ group.

Pectins are especially sold by the company Cargill under the name Unipectine™, by the company CP-Kelco under the name Genu, and by Danisco under the name Grinsted Pectin.

Other Polysaccharides

Among the other polysaccharides that may be used according to the invention, mention may also be made of chitin (poly-N-acetyl-D-glucosamine, β(1,4)-2-acetamido-2-deoxy-D-glucose), chitosan and derivatives (chitosan-beta-glycerophosphate, carboxymethylchitin, etc.) such as those sold by the company France-Chitine; glycosaminoglycans (GAG) such as hyaluronic acid, chondroitin sulfate, dermatan sulfate, keratan sulfate, and preferably hyaluronic acid; xylans (or arabinoxylans) and derivatives.

Arabinoxylans are polymers of xylose and arabinose, all grouped under the name pentosans.

Xylans consist of a main chain of β(1,4) linked D-xylose units on which are found three substituents (Rouau & Thibault, 1987): acid units, a-L-arabinofuranose units, side chains which may contain arabinose, xylose, galactose and glucuronic acid.

According to this variant, the polysaccharide is preferably hyaluronic acid, or a salt thereof such as the sodium salt (sodium hyaluronate).

II. Synthetic Polymeric Gelling Agents

For the purposes of the invention, the term "synthetic" means that the polymer is neither naturally existing nor a derivative of a polymer of natural origin.

The synthetic polymeric hydrophilic gelling agent under consideration according to the invention may or may not be particulate.

For the purposes of the invention, the term "particulate" means that the polymer is in the form of particles, preferably spherical particles.

As emerges from the text hereinbelow, the polymeric hydrophilic gelling agent is advantageously chosen from crosslinked acrylic homopolymers or copolymers; associative polymers, in particular associative polymers of polyurethane type; polyacrylamides and crosslinked and/or neutralized 2-acrylamido-2-methylpropanesulfonic acid polymers and copolymers; modified or unmodified carboxyvinyl polymers, and mixtures thereof, especially as defined below.

According to a preferred embodiment, the hydrophilic gelling agent is chosen from synthetic polymeric gelling agents, and preferably from associative polymers, polyacrylamides, 2-acrylamido-2-methylpropanesulfonic acid polymers and copolymers, and carboxyvinyl polymers, and more preferentially from 2-acrylamido-2-methylpropanesulfonic acid polymers and copolymers.

II.A. Particulate Synthetic Polymeric Gelling Agents

They are preferably chosen from crosslinked polymers.

They may especially be crosslinked acrylic homopolymers or copolymers, which are preferably partially neutralized or neutralized, and which are in particulate form.

According to one embodiment, the particulate gelling agent according to the present invention is chosen from crosslinked sodium polyacrylates. Preferably, it has in the dry or non-hydrated state a mean size of less than or equal to 100 μm and preferably less than or equal to 50 μm. The mean size of the particles corresponds to the mass-average diameter (D50) measured by laser particle size analysis or another equivalent method known to those skilled in the art.

Thus, preferably, the particulate gelling agent according to the present invention is chosen from crosslinked sodium polyacrylates, preferably in the form of particles with a mean size (or mean diameter) of less than or equal to 100 microns, more preferably in the form of spherical particles.

As examples of crosslinked sodium polyacrylates, mention may be made of those sold under the brand names Octacare X100, X110 and RM100 by the company Avecia, those sold under the names Flocare GB300 and Flosorb 500 by the company SNF, those sold under the names Luquasorb 1003, Luquasorb 1010, Luquasorb 1280 and Luquasorb 1110 by the company BASF, those sold under the names Water Lock G400 and G430 (INCI name: Acrylamide/Sodium acrylate copolymer) by the company Grain Processing.

Mention may also be made of crosslinked polyacrylate microspheres, for instance those sold under the name Aquakeep® 10 SH NF by the company Sumitomo Seika.

Such gelling agents may be used in a proportion of from 0.1% to 5% by weight of solids relative to the total weight of the aqueous phase, especially from 0.5% to 2% by weight and in particular in a proportion of about from 0.8% to 1.7% by weight, relative to the total weight of the aqueous phase.

II.B. Non-Particulate Synthetic Polymeric Gelling Agents

This family of gelling agents may be detailed under the following subfamilies: 1. Associative polymers, 2. Polyacrylamides and crosslinked and/or neutralized 2-acrylamido-2-methylpropanesulfonic acid polymers and copolymers, and 3. Modified or unmodified carboxyvinyl polymers.

II.B.1 Associative Polymers

For the purposes of the present invention, the term "associative polymer" means any amphiphilic polymer comprising in its structure at least one fatty chain and at least one hydrophilic portion. The associative polymers in accordance with the present invention may be anionic, cationic, nonionic or amphoteric.

Associative Anionic Polymers

Among the associative anionic polymers that may be mentioned are those comprising at least one hydrophilic unit, and at least one fatty-chain allyl ether unit, more particularly those whose hydrophilic unit is formed by an unsaturated ethylenic anionic monomer, more particularly by a vinylcarboxylic acid and most particularly by an acrylic acid or a methacrylic acid or mixtures thereof, and whose fatty-chain allyl ether unit corresponds to the monomer of formula (I) below:

$$CH_2=C(R')CH_2 \, O \, B_n R \quad (I)$$

in which R' denotes H or CH3, B denotes an ethylenoxy radical, n is zero or denotes an integer ranging from 1 to 100, R denotes a hydrocarbon-based radical chosen from alkyl, arylalkyl, aryl, alkylaryl and cycloalkyl radicals, containing from 8 to 30 carbon atoms, preferably 10 to 24 carbon atoms and even more particularly from 12 to 18 carbon atoms.

Anionic amphiphilic polymers of this type are described and prepared, according to an emulsion polymerization process, in patent EP 0 216 479.

Among the associative anionic polymers that may also be mentioned are maleic anhydride/$C_{30}$-$C_{38}$ α-olefin/alkyl maleate terpolymers, such as the product (maleic anhydride/$C_{30}$-$C_{38}$ α-olefin/isopropyl maleate copolymer) sold under the name Performa V 1608 by the company Newphase Technologies.

Among the associative anionic polymers, mention may be made, according to a preferred embodiment, of copolymers comprising among their monomers an α,β-monoethylenically unsaturated carboxylic acid and an ester of an α,β-monoethylenically unsaturated carboxylic acid and of an oxyalkylenated fatty alcohol.

Preferentially, these compounds also comprise as monomer an ester of an α,β-monoethylenically unsaturated carboxylic acid and of a $C_1$-$C_4$ alcohol.

Examples of compounds of this type that may be mentioned include Aculyn 22® sold by the company Röhm & Haas, which is a methacrylic acid/ethyl acrylate/oxyalkylenated stearyl methacrylate (comprising 20 EO units) terpolymer or Aculyn 28® (methacrylic acid/ethyl acrylate/oxyethylenated behenyl methacrylate (25 EO) terpolymer).

Associative anionic polymers that may also be mentioned include anionic polymers comprising at least one hydrophilic unit of olefinic unsaturated carboxylic acid type, and at least one hydrophobic unit exclusively of ($C_{10}$-$C_{30}$)alkyl ester of unsaturated carboxylic acid type. Examples that may be mentioned include the anionic polymers described and prepared according to U.S. Pat. Nos. 3,915,921 and 4,509, 949.

Associative anionic polymers that may also be mentioned include anionic terpolymers.

The anionic terpolymer used according to the invention is a linear or branched and/or crosslinked terpolymer, of at least one monomer (1) bearing an acid function in free form, which is partially or totally salified with a nonionic monomer (2) chosen from N,N-dimethylacrylamide and 2-hydroxyethyl acrylate and at least one polyoxyethylenated alkyl acrylate monomer (3) of formula (1) below:

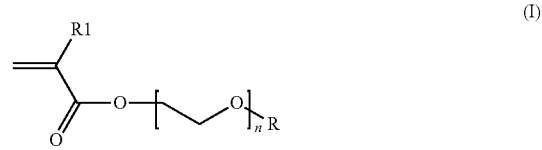

in which R1 represents a hydrogen atom, R represents a linear or branched $C_2$-$C_8$ alkyl radical and n represents a number ranging from 1 to 10.

The term "branched polymer" denotes a non-linear polymer which bears pendent chains so as to obtain, when this polymer is dissolved in water, a high degree of entanglement leading to very high viscosities, at a low speed gradient.

The term "crosslinked polymer" denotes a non-linear polymer which is in the form of a three-dimensional network that is insoluble in water but swellable in water, leading to the production of a chemical gel.

The acid function of the monomer (1) is especially a sulfonic acid or phosphonic acid function, said functions being in free or partially or totally salified form.

The monomer (1) may be chosen from styrenesulfonic acid, ethylsulfonic acid and 2-methyl-2-[(1-oxo-2-propenyl]amino]-1-propanesulfonic acid (also known as acryloyldimethyl taurate), in free or partially or totally salified form. It is present in the anionic terpolymer preferably in molar proportions of between 5 mol % and 95 mol % and more particularly between 10 mol % and 90 mol %. The monomer (1) will more particularly be 2-methyl-2-[(1-oxo-2-propenyl)amino]-1-propanesulfonic acid in free or partially or totally salified form.

The acid function in partially or totally salified form will preferably be an alkali metal salt such as a sodium or potassium salt, an ammonium salt, an amino alcohol salt such as a monoethanolamine salt, or an amino acid salt such as a lysine salt.

The monomer (2) is preferably present in the anionic terpolymer in molar proportions of between 4.9 mol % and 90 mol %, more particularly between 9.5 mol % and 85 mol % and even more particularly between 19.5 mol % and 75 mol %.

In formula (I), examples of linear C8-C16 alkyl radicals that may be mentioned include octyl, decyl, undecyl, tridecyl, tetradecyl, pentadecyl and hexadecyl.

In formula (I), examples of branched C8-C16 alkyl radicals that may be mentioned include 2-ethylhexyl, 2-propylheptyl, 2-butyloctyl, 2-pentylnonyl, 2-hexyldecyl, 4-methylpentyl, 5-methylhexyl, 6-methylheptyl, 15-methylpentadecyl, 16-methylheptadecyl and 2-hexyloctyl.

According to a particular form of the invention, in formula (I), R denotes a $C_{12}$-$C_{16}$ alkyl radical.

According to a particular form of the invention, in formula (I), n ranges from 3 to 5.

Tetraethoxylated lauryl acrylate will more particularly be used as monomer of formula (I).

The monomer (3) of formula (I) is preferably present in the anionic terpolymer in molar proportions of between 0.1 mol % and 10 mol % and more particularly between 0.5 mol % and 5 mol %.

According to a particular mode of the invention, the anionic terpolymer is crosslinked and/or branched with a diethylenic or polyethylenic compound in the proportion expressed relative to the total amount of monomers used, from 0.005 mol % to 1 mol %, preferably from 0.01 mol % to 0.5 mol % and more particularly from 0.01 mol % to 0.25 mol %.

The crosslinking agent and/or branching agent is preferably chosen from ethylene glycol dimethacrylate, diallyloxyacetic acid or a salt thereof, such as sodium diallyloxyacetate, tetraallyloxyethane, ethylene glycol diacrylate, diallylurea, triallylamine, trimethylolpropane triacrylate and methylenebis(acrylamide), or mixtures thereof.

The anionic terpolymer may contain additives such as complexing agents, transfer agents or chain-limiting agents.

Use will be made more particularly of an anionic terpolymer of 2-methyl-2-[(1-oxo-2-propenyl)amino]-1-propanesulfonic acid partially or totally salified in the form of the ammonium salt, N,N-dimethylacrylamide and tetraethoxylated lauryl acrylate crosslinked with trimethylolpropane triacrylate, of INCI name Polyacrylate Crosspolymer-6, such as the product sold under the trade name Sepimax Zen® by the company SEPPIC.

Cationic Associative Polymers

Cationic associative polymers that may be mentioned include polyacrylates bearing amine side groups.

The polyacrylates bearing quaternized or non-quaternized amine side groups contain, for example, hydrophobic groups of the type such as steareth-20 (polyoxyethylenated (20) stearyl alcohol).

Examples of polyacrylates bearing amino side chains that may be mentioned are the polymers 8781-121B or 9492-10$^3$ from the company National Starch.

Nonionic Associative Polymers

The nonionic associative polymers may be chosen from:
copolymers of vinylpyrrolidone and of fatty-chain hydrophobic monomers;
copolymers of $C_1$-$C_6$ alkyl methacrylates or acrylates and of amphiphilic monomers comprising at least one fatty chain;
copolymers of hydrophilic methacrylates or acrylates and of hydrophobic monomers comprising at least one fatty chain, for instance the polyethylene glycol methacrylate/lauryl methacrylate copolymer;
associative polyurethanes.

Associative polyurethanes are nonionic block copolymers comprising in the chain both hydrophilic blocks usually of polyoxyethylene nature (referred to as polyether polyurethanes), and hydrophobic blocks that may be aliphatic sequences alone and/or cycloaliphatic and/or aromatic sequences.

In particular, these polymers comprise at least two hydrocarbon-based lipophilic chains containing from 6 to 30 carbon atoms, separated by a hydrophilic block, the hydrocarbon-based chains possibly being pendent chains or chains at the end of the hydrophilic block. In particular, it is possible for one or more pendent chains to be envisaged. In addition, the polymer may comprise a hydrocarbon-based chain at one end or at both ends of a hydrophilic block.

Associative polyurethanes may be block polymers, in triblock or multiblock form. The hydrophobic blocks may thus be at each end of the chain (for example: triblock copolymer containing a hydrophilic central block) or distributed both at the ends and in the chain (for example: multiblock copolymer). These polymers may also be graft polymers or star polymers. Preferably, the associative polyurethanes are triblock copolymers in which the hydrophilic block is a polyoxyethylene chain comprising from 50 to 1000 oxyethylene groups. In general, associative polyurethanes comprise a urethane bond between the hydrophilic blocks, whence arises the name.

According to one preferred embodiment, a nonionic associative polymer of polyurethane type is used as gelling agent.

As examples of nonionic fatty-chain polyurethane polyethers that may be used in the invention, it is also possible to use Rheolate® FX 1100 (Steareth-100/PEG 136/HDI (hexamethyl diisocyanate) copolymer), Rheolate® 205 containing a urea function, sold by the company Elementis, or Rheolate® 208, 204 or 212, and also Acrysol® RM 184 or Acrysol® RM 2020.

Mention may also be made of the product Elfacos® T210 containing a C12-C14 alkyl chain, and the product Elfacos® T212 containing a C16-18 alkyl chain (PPG-14 Palmeth-60 Hexyl Dicarbamate), from Akzo.

The product DW 1206B® from Rohm & Haas containing a C20 alkyl chain and a urethane bond, sold at a solids content of 20% in water, may also be used.

Use may also be made of solutions or dispersions of these polymers, especially in water or in aqueous/alcoholic medium. Examples of such polymers that may be mentioned are Rheolate® 255, Rheolate® 278 and Rheolate® 244 sold by the company Elementis. The products DW 1206F and DW 1206J sold by the company Rohm & Haas may also be used.

The associative polyurethanes that may be used according to the invention are in particular those described in the article by G. Fonnum, J. Bakke and Fk. Hansen, Colloid Polym. Sci., 271, 380-389 (1993).

Even more particularly, according to the invention, use may also be made of an associative polyurethane that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate.

Such polyurethane polyethers are sold in particular by the company Röhm & Haas under the names Aculyn® 46 and Aculyn® 44. Aculyn® 46 is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%), and Aculyn® 44 is a polycondensate of polyethylene glycol containing 150 or 180 mol of ethylene oxide, of decyl alcohol and of methylenebis(4-cyclohexyl isocyanate) (SMDI), at 35% by weight in a mixture of propylene glycol (39%) and water (26%).

Use may also be made of solutions or dispersions of these polymers, especially in water or in aqueous/alcoholic medium. Examples of such polymers that may be mentioned include SER AD FX1010, SER AD FX1035 and SER AD 107 from the company Elementis, and Rheolate® 255, Rheolate® 278 and Rheolate® 244 sold by the company Elementis. Use may also be made of the products Aculyn® 44, Aculyn® 46, DW 1206F and DW 1206J, and also Acrysol® RM 184 from the company Röhm & Haas, or alternatively Borchigel LW 44 from the company Borchers, and mixtures thereof.

Amphoteric Associative Polymers

Among the associative amphoteric polymers of the invention, mention may be made of crosslinked or non-crosslinked, branched or unbranched amphoteric polymers, which may be obtained by copolymerization:

1) of at least one monomer of formula (IVa) or (IVb):

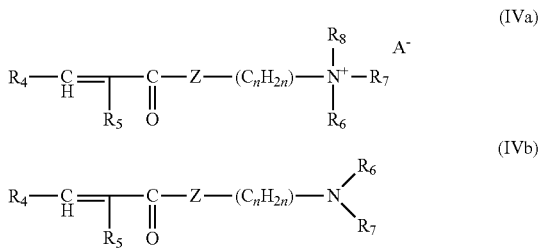

in which:
- $R_4$ and $R_5$, which may be identical or different, represent a hydrogen atom or a methyl radical;
- $R_6$, $R_7$ and $R_8$, which may be identical or different, represent a linear or branched alkyl radical containing from 1 to 30 carbon atoms;
- Z represents an NH group or an oxygen atom;
- n is an integer from 2 to 5;
- $A^-$ is an anion derived from an organic or mineral acid, such as a methosulfate anion or a halide such as chloride or bromide;

2) of at least one monomer of formula (V):

in which $R_9$ and $R_{10}$, which may be identical or different, represent a hydrogen atom or a methyl radical and Z1 represents a group OH or a group $NHC(CH_3)_2CH_2SO_3H$;

3) of at least one monomer of formula (VI):

in which $R_9$ and $R_{10}$, which may be identical or different, represent a hydrogen atom or a methyl radical, X denotes an oxygen or nitrogen atom and $R_{11}$ denotes a linear or branched alkyl radical containing from 1 to 30 carbon atoms;

4) optionally at least one crosslinking or branching agent;

at least one of the monomers of formula (IVa), (IVb) or (VI) comprising at least one fatty chain containing from 8 to 30 carbon atoms and said compounds of the monomers of formulae (IVa), (IVb), (V) and (VI) possibly being quaternized, for example with a $C_1$-$C_4$ alkyl halide or a $C_1$-$C_4$ dialkyl sulfate.

The monomers of formulae (IVa) and (IVb) of the present invention are preferably chosen from the group consisting of:
- dimethylaminoethyl methacrylate, dimethylaminoethyl acrylate,
- diethylaminoethyl methacrylate, diethylaminoethyl acrylate,
- dimethylaminopropyl methacrylate, dimethylaminopropyl acrylate,
- dimethylaminopropylmethacrylamide, dimethylaminopropylacrylamide, which are optionally quaternized, for example with a $C_1$-$C_4$ alkyl halide or a $C_1$-$C_4$ dialkyl sulfate.

More particularly, the monomer of formula (IVa) is chosen from acrylamidopropyltrimethylammonium chloride and methacrylamidopropyltrimethylammonium chloride.

The compounds of formula (V) of the present invention are preferably chosen from the group formed by acrylic acid, methacrylic acid, crotonic acid, 2-methylcrotonic acid, 2-acrylamido-2-methylpropanesulfonic acid and 2-methacrylamido-2-methylpropanesulfonic acid. More particularly, the monomer of formula (V) is acrylic acid.

The monomers of formula (VI) of the present invention are preferably chosen from the group formed by $C_{12}$-$C_{22}$ and more particularly $C_{16}$-$C_{18}$ alkyl acrylates or methacrylates.

The crosslinking or branching agent is preferably chosen from N,N'-methylenebisacrylamide, triallylmethylammonium chloride, allyl methacrylate, n-methylolacrylamide, polyethylene glycol dimethacrylates, ethylene glycol dimethacrylate, diethylene glycol dimethacrylate, 1,6-hexanediol dimethacrylate and allyl sucrose.

The polymers according to the invention may also contain other monomers such as nonionic monomers and in particular $C_1$-$C_4$ alkyl acrylates or methacrylates.

The ratio of the number of cationic charges/anionic charges in these amphoteric polymers is preferably equal to about 1.

The weight-average molecular weights of the associative amphoteric polymers represents a weight-average molecular mass of greater than 500, preferably of between 10 000 and 10 000 000 and even more preferentially between 100 000 and 8 000 000.

Preferably, the associative amphoteric polymers of the invention contain from 1 mol % to 99 mol %, more preferentially from 20 mol % to 95 mol % and even more preferentially from 25 mol % to 75 mol % of compound(s) of formula (IVa) or (IVb). They also preferably contain from 1 mol % to 80 mol %, more preferentially from 5 mol % to 80 mol % and even more preferentially from 25 mol % to 75 mol % of compound(s) of formula (V). The content of compound(s) of formula (VI) is preferably between 0.1 mol % and 70 mol %, more preferentially between 1 mol % and 50 mol % and even more preferentially between 1 mol % and 10 mol %. The crosslinking or branching agent, when it is present, is preferably between 0.0001 mol % and 1 mol % and even more preferentially between 0.0001 mol % and 0.1 mol %.

Preferably, the mole ratio between the compound(s) of formula (Wa) or (Wb) and the compound(s) of formula (V) ranges from 20/80 to 95/5 and more preferentially from 25/75 to 75/25.

The associative amphoteric polymers according to the invention are described, for example, in patent application WO 98/44012.

The amphoteric polymers that are particularly preferred according to the invention are chosen from acrylic acid/acrylamidopropyltrimethylammonium chloride/stearyl methacrylate copolymers.

According to a preferred embodiment, the associative polymer is chosen from nonionic associative polymers and more particularly from associative polyurethanes, such as Steareth-100/PEG-136/HDI Copolymer sold under the name Rheolate FX 1100 by Elementis.

Such an associative polymer is advantageously used in a proportion of from 0.1% to 8% by weight of solids and preferably between 0.5% and 4% by weight, relative to the total weight of the aqueous phase.

II.B.2 Polyacrylamides and 2-acrylamido-2-methylpropanesulfonic Acid Polymers and Copolymers The polymers used that are suitable as aqueous gelling agent for the invention may be crosslinked or non-crosslinked homopolymers or copolymers comprising at least the 2-acrylamidomethylpropanesulfonic acid (AMPS®) monomer, in a form partially or totally neutralized with a mineral base other than aqueous ammonia, such as sodium hydroxide or potassium hydroxide.

They are preferably totally or almost totally neutralized, i.e. at least 90% neutralized.

These AMPS® polymers according to the invention may be crosslinked or non-crosslinked.

When the polymers are crosslinked, the crosslinking agents may be chosen from the polyolefinically unsaturated compounds commonly used for crosslinking polymers obtained by radical polymerization.

Examples of crosslinking agents that may be mentioned include divinylbenzene, diallyl ether, dipropylene glycol diallyl ether, polyglycol diallyl ethers, triethylene glycol divinyl ether, hydroquinone diallyl ether, ethylene glycol or tetraethylene glycol di(meth)acrylate, trimethylolpropane triacrylate, methylenebisacrylamide, methylenebismethacrylamide, triallylamine, triallyl cyanurate, diallyl maleate, tetraallylethylenediamine, tetraallyloxyethane, trimethylolpropane diallyl ether, allyl (meth)acrylate, allylic ethers of alcohols of the sugar series, or other allyl or vinyl ethers of polyfunctional alcohols, and also the allylic esters of phosphoric and/or vinylphosphonic acid derivatives, or mixtures of these compounds.

According to one preferred embodiment of the invention, the crosslinking agent is chosen from methylenebisacrylamide, allyl methacrylate and trimethylolpropane triacrylate (TMPTA). The degree of crosslinking generally ranges from 0.01 mol % to 10 mol % and more particularly from 0.2 mol % to 2 mol % relative to the polymer.

The AMPS® polymers that are suitable for use in the invention are water-soluble or water-dispersible. In this case, they are:

either "homopolymers" comprising only AMPS monomers and, if they are crosslinked, one or more crosslinking agents such as those defined above;

or copolymers obtained from AMPS® and from one or more hydrophilic or hydrophobic ethylenically unsaturated monomers and, if they are crosslinked, one or more crosslinking agents such as those defined above. When said copolymers comprise hydrophobic ethylenically unsaturated monomers, these monomers do not comprise a fatty chain and are preferably present in small amounts.

For the purpose of the present invention, the term "fatty chain" means any hydrocarbon-based chain comprising at least 7 carbon atoms.

The term "water-soluble or water-dispersible" means polymers which, when introduced into an aqueous phase at 25° C., at a mass concentration equal to 1%, make it possible to obtain a macroscopically homogeneous and transparent solution, i.e. a solution with a maximum light transmittance value, at a wavelength equal to 500 nm, through a sample 1 cm thick, of at least 60% and preferably of at least 70%.

The "homopolymers" according to the invention are preferably crosslinked and neutralized, and they may be obtained according to the preparation process comprising the following steps:

(a) the monomer such as AMPS in free form is dispersed or dissolved in a solution of tert-butanol or of water and tert-butanol;

(b) the monomer solution or dispersion obtained in (a) is neutralized with one or more mineral or organic bases, preferably aqueous ammonia $NH_3$, in an amount making it possible to obtain a degree of neutralization of the sulfonic acid functions of the polymer ranging from 90% to 100%;

(c) the crosslinking monomer(s) are added to the solution or dispersion obtained in (b);

(d) a standard free-radical polymerization is performed in the presence of free-radical initiators at a temperature ranging from 10° C. to 150° C.; the polymer precipitates in the tert-butanol-based solution or dispersion.

The water-soluble or water-dispersible AMPS® copolymers according to the invention contain water-soluble ethylenically unsaturated monomers, hydrophobic monomers, or mixtures thereof.

The water-soluble comonomers may be ionic or nonionic.

Among the ionic water-soluble comonomers, examples that may be mentioned include the following compounds, and salts thereof:

(meth)acrylic acid,
styrenesulfonic acid,
vinylsulfonic acid and (meth)allylsulfonic acid,
vinylphosphonic acid,
maleic acid,
itaconic acid,
crotonic acid,
water-soluble vinyl monomers of formula (A) below:

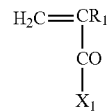

(A)

in which:
$R_1$ is chosen from H, $-CH_3$, $-C_2H_5$ and $-C_3H_7$,
$X_1$ is chosen from:
alkyl oxides of type $-OR_2$ where $R_2$ is a linear or branched, saturated or unsaturated hydrocarbon-based radical containing from 1 to 6 carbon atoms, substituted with at least one sulfonic ($-SO_3^-$) and/or sulfate ($-SO_4^-$) and/or phosphate ($-PO_4H_2^-$) group.

Among the nonionic water-soluble comonomers, examples that may be mentioned include:
(meth)acrylamide,
N-vinylacetamide and N-methyl-N-vinylacetamide,
N-vinylformamide and N-methyl-N-vinylformamide,
-maleic anhydride,
vinylamine,
N-vinyllactams comprising a cyclic alkyl group containing from 4 to 9 carbon atoms, such as N-vinylpyrrolidone, N-butyrolactam and N-vinylcaprolactam,
vinyl alcohol of formula $CH_2=CHOH$,
water-soluble vinyl monomers of formula (B) below:

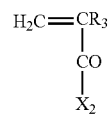

(B)

in which:
R$_3$ is chosen from H, —CH$_3$, —C$_2$H$_5$ and —C$_3$H$_7$,
X2 is chosen from alkyl oxides of the type —OR$_4$ where R$_4$ is a linear or branched, saturated or unsaturated hydrocarbon-based radical containing from 1 to 6 carbon atoms, optionally substituted with a halogen (iodine, bromine, chlorine or fluorine) atom; a hydroxyl (—OH) group; ether.

Mention is made, for example, of glycidyl (meth)acrylate, hydroxyethyl methacrylate, and (meth)acrylates of ethylene glycol, of diethylene glycol or of polyalkylene glycol.

Among the hydrophobic co-monomers without a fatty chain, mention may be made, for example, of:
styrene and derivatives thereof, such as 4-butylstyrene, α-methylstyrene and vinyltoluene;
vinyl acetate of formula CH$_2$=CH—OCOCH$_3$;
vinyl ethers of formula CH$_2$=CHOR in which R is a linear or branched, saturated or unsaturated hydrocarbon-based radical containing from 1 to 6 carbons;
acrylonitrile;
caprolactone;
vinyl chloride and vinylidene chloride;
silicone derivatives, which, after polymerization, result in silicone polymers such as methacryloxypropyltris(trimethylsiloxy)silane and silicone methacrylamides;
hydrophobic vinyl monomers of formula (C) below:

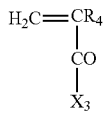

(C)

in which:
R$_4$ is chosen from H, —CH$_3$, —C$_2$H$_5$ and —C$_3$H$_7$;
X$_3$ is chosen from:
alkyl oxides of the type —OR$_5$ where R$_5$ is a linear or branched, saturated or unsaturated hydrocarbon-based radical containing from 1 to 6 carbon atoms.

Mention is made, for example, of methyl methacrylate, ethyl methacrylate, n-butyl (meth)acrylate, tert-butyl (meth)acrylate, cyclohexyl acrylate, isobornyl acrylate and 2-ethylhexyl acrylate.

The water-soluble or water-dispersible AMPS® polymers of the invention preferably have a molar mass ranging from 50 000 g/mol to 10 000 000 g/mol, preferably from 80 000 g/mol to 8 000 000 g/mol, and even more preferably from 100 000 g/mol to 7 000 000 g/mol.

As water-soluble or water-dispersible AMPS homopolymers suitable for use in the invention, mention may be made, for example, of crosslinked or non-crosslinked polymers of sodium acrylamido-2-methylpropanesulfonate, such as that used in the commercial product Simulgel 800 (CTFA name: Sodium Polyacryloyldimethyl Taurate), crosslinked ammonium acrylamido-2-methylpropanesulfonate polymers (INCI name: Ammonium Polyacryldimethyltauramide) such as those described in patent EP 0 815 928 B1 and such as the product sold under the trade name Hostacerin AMPS® by the company Clariant.

Preferably, a composition according to the invention comprises an AMPS® homopolymer.

In particular, such an AMPS® homopolymer may be present in a composition according to the invention in a content of between 0.1% and 5% by weight, preferably between 0.3% and 3% by weight and more preferentially between 0.5% and 2.5% by weight relative to the total weight of the composition.

As water-soluble or water-dispersible AMPS copolymers in accordance with the invention, examples that may be mentioned include:
crosslinked acrylamide/sodium acrylamido-2-methylpropanesulfonate copolymers, such as that used in the commercial product Sepigel 305 (CTFA name: Polyacrylamide/C$_{13}$-C$_{14}$ Isoparaffin/Laureth-7) or that used in the commercial product sold under the name Simulgel 600 (CTFA name: Acrylamide/Sodium acryloyldimethyltaurate/Isohexadecane/Polysorbate-80) by the company SEPPIC;
copolymers of AMPS® and of vinylpyrrolidone or vinylformamide, such as that used in the commercial product sold under the name Aristoflex AVC® by the company Clariant (CTFA name: Ammonium Acryloyldimethyltaurate/VP copolymer) but neutralized with sodium hydroxide or potassium hydroxide;
copolymers of AMPS® and of sodium acrylate, for instance the AMPS/sodium acrylate copolymer, such as that used in the commercial product sold under the name Simulgel EG® by the company SEPPIC or under the trade name Sepinov EM (CTFA name: Hydroxyethyl acrylate/Sodium acryloyldimethyltaurate copolymer);
copolymers of AMPS® and of hydroxyethyl acrylate, for instance the AMPS®/hydroxyethyl acrylate copolymer, such as that used in the commercial product sold under the name Simulgel NS® by the company SEPPIC (CTFA name: Hydroxyethyl acrylate/sodium acryloyldimethyltaurate copolymer (and) squalane (and) polysorbate 60), or such as the product sold under the name Sodium acrylamido-2-methylpropanesulfonate/hydroxyethyl acrylate copolymer, such as the commercial product Sepinov EMT 10 (INCI name: Hydroxyethyl acrylate/Sodium acryloyldimethyltaurate copolymer).

As preferred water-soluble or water-dispersible AMPS copolymers in accordance with the invention, mention may be made of copolymers of AMPS® and of hydroxyethyl acrylate.

In general, a composition according to the invention may comprise from 0.1% to 8% by weight, preferably from 0.2% to 5% by weight and more preferentially from 0.7% to 5% by weight of solids of polyacrylamide(s) and/or of crosslinked and/or neutralized 2-acrylamido-2-methylpropanesulfonic acid polymer(s) and copolymer(s) relative to the total weight of the composition.

II.B.3 Modified or Unmodified Carboxyvinyl Polymers

The modified or unmodified carboxyvinyl polymers may be copolymers derived from the polymerization of at least one monomer (a) chosen from α,β-ethylenically unsaturated carboxylic acids or esters thereof, with at least one ethylenically unsaturated monomer (b) comprising a hydrophobic group.

The term "copolymers" means both copolymers obtained from two types of monomer and those obtained from more than two types of monomer, such as terpolymers obtained from three types of monomer.

Their chemical structure more particularly comprises at least one hydrophilic unit and at least one hydrophobic unit. The term "hydrophobic group or unit" means a radical with a saturated or unsaturated, linear or branched hydrocarbon-based chain, comprising at least 8 carbon atoms, preferably from 10 to 30 carbon atoms, in particular from 12 to 30 carbon atoms and more preferentially from 18 to 30 carbon atoms.

Preferably, these copolymers are chosen from copolymers derived from the polymerization:

of at least one monomer of formula (1) below:

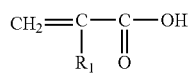

(1)

in which $R_1$ denotes H or $CH_3$ or $C_2H_5$, i.e. acrylic acid, methacrylic acid or ethacrylic acid monomers, and of at least one monomer of unsaturated carboxylic acid $(C_{10}$-$C_{30})$alkyl ester type corresponding to the monomer of formula (2) below:

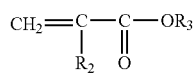

(2)

in which $R_2$ denotes H or $CH_3$ or $C_2H_5$ (i.e. acrylate, methacrylate or ethacrylate units) and preferably H (acrylate units) or $CH_3$ (methacrylate units), $R_3$ denoting a $C_{10}$-$C_{30}$ and preferably $C_{12}$-$C_{22}$ alkyl radical.

The unsaturated carboxylic acid $(C_{10}$-$C_3O)$alkyl esters are preferably chosen from lauryl acrylate, stearyl acrylate, decyl acrylate, isodecyl acrylate and dodecyl acrylate, and the corresponding methacrylates, such as lauryl methacrylate, stearyl methacrylate, decyl methacrylate, isodecyl methacrylate and dodecyl methacrylate, and mixtures thereof.

According to a preferred embodiment, these polymers are crosslinked.

Among the copolymers of this type that will be used more particularly are polymers derived from the polymerization of a monomer mixture comprising:

essentially acrylic acid, an ester of formula (2) described above in which $R_2$ denotes H or $CH_3$, $R_3$ denoting an alkyl radical containing from 12 to 22 carbon atoms, and a crosslinking agent, which is a well-known copolymerizable unsaturated polyethylenic monomer, for instance diallyl phthalate, allyl (meth)acrylate, divinylbenzene, (poly)ethylene glycol dimethacrylate and methylenebisacrylamide.

Among the copolymers of this type, use will more particularly be made of those consisting of from 95% to 60% by weight of acrylic acid (hydrophilic unit), 4% to 40% by weight of $C_{10}$-$C_{30}$ alkyl acrylate (hydrophobic unit) and 0% to 6% by weight of crosslinking polymerizable monomer, or alternatively those consisting of from 98% to 96% by weight of acrylic acid (hydrophilic unit), 1% to 4% by weight of $C_{10}$-$C_{30}$ alkyl acrylate (hydrophobic unit) and 0.1% to 0.6% by weight of crosslinking polymerizable monomer such as those described previously.

Among the abovementioned polymers, the ones that are most particularly preferred according to the present invention are acrylate/$C_{10}$-$C_{30}$-alkyl acrylate copolymers (INCI name: Acrylates/$C_{10-30}$ Alkyl acrylate Crosspolymer) such as the products sold by the company Lubrizol under the trade names Pemulen TR-1, Pemulen TR-2, Carbopol 1382, Carbopol EDT 2020 and Carbopol Ultrez 20 Polymer, and even more preferentially Pemulen TR-2.

Among the modified or unmodified carboxyvinyl polymers, mention may also be made of sodium polyacrylates such as those sold under the name Cosmedia SP® containing 90% solids and 10% water, or Cosmedia SPL® as an inverse emulsion containing about 60% solids, an oil (hydrogenated polydecene) and a surfactant (PPG-5 Laureth-5), both sold by the company Cognis.

Mention may also be made of partially neutralized sodium polyacrylates that are in the form of an inverse emulsion comprising at least one polar oil, for example the product sold under the name Luvigel® EM by the company BASF.

The modified or unmodified carboxyvinyl polymers may also be chosen from crosslinked (meth)acrylic acid homopolymers.

For the purposes of the present patent application, the term "(meth)acrylic" means "acrylic or methacrylic".

Examples that may be mentioned include the products sold by Lubrizol under the names Carbopol 910, 934, 940, 941, 934 P, 980, 981, 2984, 5984 and Carbopol Ultrez 10 Polymer, or by 3V-Sigma under the name Synthalen® K, Synthalen® L or Synthalen® M.

Among the modified or unmodified carboxyvinyl polymers, mention may be made in particular of Carbopol (INCI name: carbomer) and Pemulen (CTFA name: Acrylates/$C_{10-30}$ alkyl acrylate crosspolymer) sold by the company Lubrizol.

The modified or unmodified carboxyvinyl polymers may be present in a proportion of from 0.1% to 5% by weight of solids relative to the weight of the aqueous phase, in particular from 0.3% to 1% by weight and preferably between 0.4% and 1% by weight, relative to the weight of the aqueous phase.

Advantageously, a composition according to the invention comprises a synthetic polymeric hydrophilic gelling agent chosen from 2-acrylamido-2-methylpropanesulfonic acid polymers and copolymers.

According to a preferred variant, the synthetic polymeric hydrophilic gelling agent is an AMPS® homopolymer.

III. Other Hydrophilic Gelling Agents

These gelling agents are more particularly chosen from mixed silicates and fumed silicas.

III.A. Mixed Silicate

For the purposes of the present invention, the term "mixed silicate" means all silicates of natural or synthetic origin containing several (two or more) types of cations chosen from alkali metals (for example Na, Li, K) or alkaline-earth metals (for example Be, Mg, Ca), transition metals and aluminium.

According to a particular embodiment, the mixed silicate(s) are in the form of solid particles containing at least 10% by weight of at least one silicate relative to the total weight of the particles. In the rest of the present description, these particles are referred to as "silicate particles".

Preferably, the silicate particles contain less than 1% by weight of aluminium relative to the total weight of the particles. Even more preferably, they contain from 0% to 1% by weight of aluminium relative to the total weight of the particles.

Preferably, the silicate particles contain at least 50% by weight of silicate and better still at least 70% by weight relative to the total weight of the particles. Particles containing at least 90% by weight of silicates, relative to the total weight of the particles, are particularly preferred.

In particular, it is an alkali metal or alkaline-earth metal, aluminium or iron silicate or mixture of silicates.

Preferably, it is sodium, magnesium and/or lithium silicate.

To ensure good cosmetic properties, these silicates are generally in a finely divided form, and in particular in the form of particles with a mean size ranging from 2 nm to 1 µm (from 2 nm to 1000 nm), preferably from 5 nm to 600 nm and even more preferentially from 20 to 250 nm.

The silicate particles may have any form, for example the form of spheres, flakes, needles, platelets, discs, leaflets, or totally random forms. Preferably, the silicate particles are in the form of discs or leaflets.

Thus, the term "mean size" of the particles means the numerical mean size of the largest dimension (length) that it is possible to measure between two diametrically opposite points on an individual particle. The size may be determined, for example, by transmission electron microscopy or by measuring the specific surface area via the BET method or with a laser particle size analyser.

When the particles are in the form of discs or leaflets, they generally have a thickness ranging from about 0.5 nm to 5 nm.

The silicate particles may consist of an alloy with metal or metalloid oxides, obtained, for example, by thermal melting of the various constituents thereof. When the particles also comprise such a metal or metalloid oxide, this oxide is preferably chosen from silicon, boron or aluminium oxide.

According to a particular embodiment of the invention, the silicates are phyllosilicates, namely silicates having a structure in which the SiO4 tetrahedra are organized in leaflets between which the metal cations are enclosed.

The mixed silicates that are suitable for use in the invention may be chosen, for example, from montmorillonites, hectorites, bentonites, beidellite and saponites. According to a preferred embodiment of the invention, the mixed silicates used are more particularly chosen from hectorites and bentonites, and better still from laponites.

A family of silicates that is particularly preferred in the compositions of the present invention is thus the laponite family. Laponites are sodium magnesium silicates also possibly containing lithium, which have a layer structure similar to that of montmorillonites. Laponite is the synthetic form of the natural mineral known as hectorite. The synthetic origin of this family of silicates is of considerable advantage over the natural form, since it allows good control the composition of the product. In addition, laponites have the advantage of having a particle size that is much smaller than that of the natural minerals hectorite and bentonite.

Laponites that may especially be mentioned include the products sold under the following names: Laponite® XLS, Laponite® XLG, Laponite® RD, Laponite® RDS, Laponite® XL21 (these products are sodium magnesium silicates and sodium lithium magnesium silicates) by the company Rockwood Additives Limited.

Such gelling agents may be used in a proportion of from 0.1% to 8% by weight of solids relative to the total weight of the aqueous phase, especially from 0.1% to 5% by weight and in particular from 0.5% to 3% by weight, relative to the total weight of the aqueous phase.

III.B. Hydrophilic Fumed Silica

The fumed silicas according to the present invention are hydrophilic.

The hydrophilic fumed silicas are obtained by pyrolysis of silicon tetrachloride (SiCl4) in a continuous flame at 1000° C. in the presence of hydrogen and oxygen. Among the fumed silicas of hydrophilic nature that may be used according to the present invention, mention may especially be made of those sold by the company Degussa or Evonik Degussa under the trade names Aerosil® 90, 130, 150, 200, 300 and 380 or alternatively by the company Cabot under the name Carbosil H5.

Such gelling agents may be used in a proportion of from 0.1% to 10% by weight of solids relative to the total weight of the aqueous phase, especially from 0.1% to 5% by weight and in particular from 0.5% to 3% by weight, relative to the total weight of the aqueous phase.

Lipophilic Gelling Agent

For the purposes of the present invention, the term "lipophilic gelling agent" means a compound that is capable of gelling the oily phase of the compositions according to the invention.

The gelling agent is lipophilic and is thus present in the oily phase of the composition.

According to the present invention, the lipophilic gelling agent is chosen from organopolysiloxane elastomers.

The organopolysiloxane elastomer has the advantage of conferring good application properties on the composition according to the invention. It affords a very soft and mattifying feel after application, which is advantageous in particular for application to the skin. It may also allow efficient filling of the hollows present on keratin materials.

The term "organopolysiloxane elastomer" or "silicone elastomer" means a supple, deformable organopolysiloxane with viscoelastic properties and especially with the consistency of a sponge or a supple sphere. Its modulus of elasticity is such that this material withstands deformation and has a limited ability to extend and to contract. This material is capable of regaining its original shape after stretching.

It is more particularly a crosslinked organopolysiloxane elastomer.

Thus, the organopolysiloxane elastomer can be obtained by a crosslinking addition reaction of diorganopolysiloxane containing at least one hydrogen bonded to silicon and of diorganopolysiloxane having ethylenically unsaturated groups bonded to silicon, in particular in the presence of a platinum catalyst; or by a dehydrogenation crosslinking condensation reaction between a diorganopolysiloxane comprising hydroxyl end groups and a diorganopolysiloxane containing at least one hydrogen bonded to silicon, in particular in the presence of an organotin compound; or by a crosslinking condensation reaction of a diorganopolysiloxane comprising hydroxyl end groups and of a hydrolysable organopolysilane; or by thermal crosslinking of organopolysiloxane, in particular in the presence of an organic peroxide catalyst; or by crosslinking of organopolysiloxane via high-energy radiation, such as gamma rays, ultraviolet rays or an electron beam.

Preferably, the organopolysiloxane elastomer is obtained by crosslinking addition reaction (A) of diorganopolysiloxane containing at least two hydrogens each bonded to a silicon, and (B) of diorganopolysiloxane containing at least two ethylenically unsaturated groups bonded to silicon, especially in the presence (C) of a platinum catalyst, as described, for instance, in patent application EP-A-295 886.

In particular, the organopolysiloxane elastomer may be obtained by reaction of dimethylpolysiloxane bearing dimethylvinylsiloxy end groups and of methylhydrogenopolysiloxane bearing trimethylsiloxy end groups, in the presence of a platinum catalyst.

Compound (A) is the base reactant for the formation of elastomeric organopolysiloxane, and the crosslinking takes place via an addition reaction of compound (A) with compound (B) in the presence of the catalyst (C).

Compound (A) is in particular an organopolysiloxane containing at least two hydrogen atoms bonded to different silicon atoms in each molecule.

Compound (A) may have any molecular structure, especially a linear-chain or branched-chain structure or a cyclic structure.

Compound (A) may have a viscosity at 25° C. ranging from 1 to 50 000 centistokes, especially so as to be readily miscible with compound (B).

The organic groups bonded to the silicon atoms of compound (A) may be alkyl groups such as methyl, ethyl, propyl, butyl, octyl; substituted alkyl groups such as 2-phenylethyl, 2-phenylpropyl or 3,3,3-trifluoropropyl; aryl groups such as phenyl, tolyl, xylyl; substituted aryl groups such as phenylethyl; and substituted monovalent hydrocarbon-based groups such as an epoxy group, a carboxylate ester group or a mercapto group.

Compound (A) may thus be chosen from trimethylsiloxy-terminated methylhydrogenopolysiloxanes, trimethylsiloxy-terminated dimethylsiloxane/methylhydrogenosiloxane copolymers, and dimethylsiloxane/methylhydrogenosiloxane cyclic copolymers.

Compound (B) is advantageously a diorganopolysiloxane containing at least two lower alkenyl groups (for example C2-C4); the lower alkenyl group may be chosen from vinyl, allyl and propenyl groups. These lower alkenyl groups may be located in any position on the organopolysiloxane molecule, but are preferably located at the ends of the organopolysiloxane molecule. The organopolysiloxane (B) may have a branched-chain, linear-chain, cyclic or network structure, but the linear-chain structure is preferred. Compound (B) may have a viscosity ranging from the liquid state to the gum state. Preferably, compound (B) has a viscosity of at least 100 centistokes at 25° C.

Besides the abovementioned alkenyl groups, the other organic groups bonded to the silicon atoms in compound (B) may be alkyl groups such as methyl, ethyl, propyl, butyl or octyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

The organopolysiloxanes (B) can be chosen from methylvinylpolysiloxanes, methylvinylsiloxane-dimethylsiloxane copolymers, dimethylpolysiloxanes comprising dimethylvinylsiloxy end groups, dimethylsiloxane-methylphenylsiloxane copolymers comprising dimethylvinylsiloxy end groups, dimethylsiloxane-diphenylsiloxane-methylvinylsiloxane copolymers comprising dimethylvinylsiloxy end groups, dimethylsiloxane-methylvinylsiloxane copolymers comprising trimethylsiloxy end groups, dimethylsiloxane-methylphenylsiloxane-methylvinylsiloxane copolymers comprising trimethylsiloxy end groups, methyl(3,3,3-trifluoropropyl)polysiloxanes comprising dimethylvinylsiloxy end groups, and dimethylsiloxane-methyl(3,3,3-trifluoropropyl)siloxane copolymers comprising dimethylvinylsiloxy end groups.

In particular, the organopolysiloxane elastomer can be obtained by reaction of dimethylpolysiloxane comprising dimethylvinylsiloxy end groups and of methylhydropolysiloxane comprising trimethylsiloxy end groups, in the presence of a platinum catalyst.

Advantageously, the sum of the number of ethylenic groups per molecule in compound (B) and of the number of hydrogen atoms bonded to silicon atoms per molecule in compound (A) is at least 5.

It is advantageous for compound (A) to be added in an amount such that the molecular ratio between the total amount of hydrogen atoms bonded to silicon atoms in compound (A) and the total amount of all the ethylenically unsaturated groups in compound (B) is within the range from 1.5/1 to 20/1.

Compound (C) is the catalyst for the crosslinking reaction, and is especially chloroplatinic acid, chloroplatinic acid-olefin complexes, chloroplatinic acid-alkenylsiloxane complexes, chloroplatinic acid-diketone complexes, platinum black and platinum on a support.

Catalyst (C) is preferably added in an amount of from 0.1 to 1000 parts by weight and better still from 1 to 100 parts by weight, as clean platinum metal, per 1000 parts by weight of the total amount of compounds (A) and (B).

The elastomer is advantageously a non-emulsifying elastomer.

The term "non-emulsifying" defines organopolysiloxane elastomers not containing a hydrophilic chain and in particular not containing polyoxyalkylene units (especially polyoxyethylene or polyoxypropylene units) or a polyglyceryl unit. Thus, according to a specific form of the invention, the composition comprises an organopolysiloxane elastomer devoid of polyoxyalkylene units and of polyglyceryl unit.

In particular, the silicone elastomer used in the present invention is chosen from Dimethicone Crosspolymer (INCI name), Vinyl Dimethicone Crosspolymer (INCI name), Dimethicone/Vinyl Dimethicone Crosspolymer (INCI name), Dimethicone (and) Dimethicone/Vinyl Dimethicone Crosspolymer (INCI name) or Dimethicone Crosspolymer-3 (INCI name).

Preferably, the silicone elastomer used in the present invention is chosen from dimethicone (and) dimethicone/vinyl dimethicone crosspolymer.

The organopolysiloxane elastomer particles may be conveyed in the form of a gel formed from an elastomeric organopolysiloxane included in at least one hydrocarbon-based oil and/or one silicone oil. In these gels, the organopolysiloxane particles are often non-spherical particles.

Non-emulsifying elastomers are especially described in patents EP 242 219, EP 285 886 and EP 765 656 and in patent application JP-A-61-194 009.

The silicone elastomer is generally provided in the form of a gel, a paste or a powder but advantageously in the form of a gel in which the silicone elastomer is dispersed in a linear silicone oil (dimethicone) or cyclic silicone oil (e.g.: cyclopentasiloxane), advantageously in a linear silicone oil.

Non-emulsifying elastomers that may more particularly be used include those sold under the names KSG-6, KSG-15, KSG-16, KSG-18, KSG-41, KSG-42, KSG-43 and KSG-44 by the company Shin-Etsu, DC9040 and DC9041 by Dow Corning and SFE 839 by the company General Electric.

According to a particular mode, use is made of a gel of silicone elastomer dispersed in a silicone oil chosen from a non-exhaustive list comprising cyclopentadimethylsiloxane, dimethicones, dimethylsiloxanes, methyl trimethicone, phenyl methicone, phenyl dimethicone, phenyl trimethicone and cyclomethicone, preferably a linear silicone oil chosen from polydimethylsiloxanes (PDMS) or dimethicones with a viscosity at 25° C. ranging from 1 to 500 cSt, optionally modified with optionally fluorinated aliphatic groups, or with functional groups such as hydroxyl, thiol and/or amine groups.

Mention may be made especially of the compounds having the following INCI names:

dimethicone/vinyl dimethicone crosspolymer, such as USG-105 and USG-107A from the company Shin-Etsu; DC9506 and DC9701 from the company Dow Corning;

dimethicone/vinyl dimethicone crosspolymer (and) dimethicone, such as KSG-6 and KSG-16 from the company Shin-Etsu;

dimethicone/vinyl dimethicone crosspolymer (and) cyclopentasiloxane, such as KSG-15;

cyclopentasiloxane (and) dimethicone crosspolymer, such as DC9040, DC9045 and DC5930 from the company Dow Corning;

dimethicone (and) dimethicone crosspolymer, such as DC9041 from the company Dow Corning.

dimethicone (and) dimethicone crosspolymer, such as Dow Corning EL-9240® Silicone Elastomer Blend from the company Dow Corning (mixture of polydimethylsiloxane crosslinked with hexadiene/polydimethylsiloxane (2 cSt));

$C_{4-24}$ alkyl dimethicone/divinyl dimethicone crosspolymer, such as NuLastic Silk MA from the company Alzo.

Mention may in particular be made, as examples of silicone elastomers dispersed in a linear silicone oil which can advantageously be used according to the invention, of the following references:

dimethicone/vinyl dimethicone crosspolymer (and) dimethicone, such as KSG-6 and KSG-16 from the company Shin-Etsu;

dimethicone (and) dimethicone crosspolymer, such as DC9041 from the company Dow Corning; and dimethicone (and) dimethicone crosspolymer, such as Dow Corning EL-9240® Silicone Elastomer Blend from the company Dow Corning (mixture of hexadiene-crosslinked polydimethylsiloxane/polydimethylsiloxane (2 cSt)).

According to a preferred mode, the composition according to the invention comprises at least one crosslinked silicone elastomer of INCI name "dimethicone crosspolymer" or "dimethicone (and) dimethicone crosspolymer", preferably with a dimethicone whose viscosity ranges from 1 to 100 cSt and in particular from 1 to 10 cSt at 25° C., such as the mixture of hexadiene-crosslinked polydimethylsiloxane/polydimethylsiloxane (5 cSt) sold under the name DC 9041 by the company Dow Corning or the mixture of hexadiene-crosslinked polydimethylsiloxane/polydimethylsiloxane (2 cSt) sold under the name EL-9240® by the company Dow Corning.

According to a particularly preferred mode, the composition according to the invention comprises at least one crosslinked silicone elastomer of INCI name "dimethicone (and) dimethicone crosspolymer", preferably with a dimethicone whose viscosity ranges from 1 to 100 cSt and in particular from 1 to 10 cSt at 25° C., such as the mixture of hexadiene-crosslinked polydimethylsiloxane/polydimethylsiloxane (5 cSt) sold under the name DC 9041 by the company Dow Corning.

The organopolysiloxane elastomer particles may also be used in powder form: mention may be made especially of the powders sold under the names Dow Corning 9505 Powder and Dow Corning 9506 Powder by the company Dow Corning, these powders having the INCI name: dimethicone/vinyl dimethicone crosspolymer.

The organopolysiloxane powder may also be coated with silsesquioxane resin, as described, for example, in U.S. Pat. No. 5,538,793. Such elastomeric powders are sold under the names KSP-100, KSP-101, KSP-102, KSP-103, KSP-104 and KSP-105 by the company Shin-Etsu, and have the INCI name: vinyl dimethicone/methicone silsesquioxane crosspolymer.

As examples of organopolysiloxane powders coated with silsesquioxane resin that may advantageously be used according to the invention, mention may be made especially of the reference KSP-100 from the company Shin-Etsu.

Such compounds may act both as lipophilic gelling agent and as filler.

According to a first embodiment variant, if the composition according to the invention comprises an organopolysiloxane powder coated with silsesquioxane resin, it acts solely as lipophilic gelling agent. According to such an embodiment variant, a composition according to the invention comprises an organopolysiloxane powder coated with silsesquioxane resin as lipophilic gelling agent, and optionally a filler other than an organopolysiloxane powder coated with silsesquioxane resin.

According to a second embodiment variant, if the composition according to the invention comprises an organopolysiloxane powder coated with silsesquioxane resin, it acts solely as filler. According to such an embodiment variant, a composition according to the invention comprises as lipophilic gelling agent an organopolysiloxane elastomer other than an organopolysiloxane powder coated with silsesquioxane resin.

According to a third embodiment variant, if the composition according to the invention comprises an organopolysiloxane powder coated with silsesquioxane resin, it acts as lipophilic gelling agent and as filler.

As preferred lipophilic gelling agent of organopolysiloxane elastomer type, mention may be made especially of crosslinked organopolysiloxane elastomers chosen from Dimethicone Crosspolymer (INCI name), Dimethicone (and) Dimethicone Crosspolymer (INCI name), Vinyl Dimethicone Crosspolymer (INCI name), Dimethicone/Vinyl Dimethicone Crosspolymer (INCI name), Dimethicone (and) Dimethicone/Vinyl Dimethicone Crosspolymer (INCI name), Dimethicone Crosspolymer-3 (INCI name), and in particular Dimethicone (and) Dimethicone/Vinyl Dimethicone Crosspolymer (INCI name).

Preferably, a composition according to the invention comprises as lipophilic agent at least one organopolysiloxane elastomer, and preferably organopolysiloxane powder coated with silsesquioxane resin, which in particular has the INCI name: vinyl dimethicone/methicone silsesquioxane crosspolymer, and in particular the product sold under the name KSP-100 by the company Shin-Etsu.

The organopolysiloxane elastomer may be present in a composition of the present invention in a content of between 0.1% and 35% by weight, especially between 1% and 20% and more particularly between 2% and 10% by weight relative to the total weight of the composition.

Aqueous Phase

The aqueous phase of a composition according to the invention comprises water and optionally a water-soluble solvent.

In the present invention, the term "water-soluble solvent" denotes a compound that is liquid at room temperature and water-miscible (miscibility with water of greater than 50% by weight at 25° C. and atmospheric pressure).

The water-soluble solvents that may be used in the composition of the invention may also be volatile.

Among the water-soluble solvents that may be used in the composition in accordance with the invention, mention may be made especially of lower monoalcohols containing from 1 to 5 carbon atoms such as ethanol and isopropanol, glycols containing from 2 to 8 carbon atoms such as ethylene glycol, propylene glycol, 1,3-butylene glycol and dipropylene glycol, $C_3$ and $C_4$ ketones and $C_2$-$C_4$ aldehydes.

The aqueous phase (water and optionally the water-miscible solvent) may be present in the composition in a content ranging from 5% to 99%, better still from 30% to 95% by weight and preferably from 40% to 90% by weight relative to the total weight of said composition.

According to another embodiment variant, the aqueous phase of a composition according to the invention may comprise at least one $C_2$-$C_{32}$ polyol.

For the purposes of the present invention, the term "polyol" should be understood as meaning any organic molecule comprising at least two free hydroxyl groups.

Preferably, a polyol in accordance with the present invention is present in liquid form at room temperature.

A polyol that is suitable for use in the invention may be a compound of linear, branched or cyclic, saturated or unsaturated alkyl type, bearing on the alkyl chain at least two —OH functions, in particular at least three —OH functions and more particularly at least four —OH functions.

The polyols that are advantageously suitable for formulating a composition according to the present invention are those especially containing from 2 to 32 carbon atoms and preferably 3 to 16 carbon atoms.

Advantageously, the polyol may be chosen, for example, from ethylene glycol, pentaerythritol, trimethylolpropane, propylene glycol, 1,3-propanediol, butylene glycol, isoprene glycol, pentylene glycol, hexylene glycol, glycerol, polyglycerols, such as glycerol oligomers, for instance diglycerol, and polyethylene glycols, and mixtures thereof.

According to a preferred embodiment of the invention, said polyol is chosen from ethylene glycol, pentaerythritol, trimethylolpropane, propylene glycol, dipropylene glycol, glycerol, polyglycerols, polyethylene glycols and mixtures thereof.

According to a particular mode, the composition of the invention may comprise at least dipropylene glycol.

According to another particular mode, the composition of the invention may comprise at least glycerol.

Oily Phase

For the purposes of the invention, an oily phase comprises at least one oil.

The term "oil" means any fatty substance that is in liquid form at room temperature and atmospheric pressure.

An oily phase that is suitable for preparing the compositions, especially cosmetic compositions, according to the invention may comprise hydrocarbon-based oils, silicone oils, fluoro oils or non-fluoro oils, or mixtures thereof.

The oils may be volatile or non-volatile.

They may be of animal, plant, mineral or synthetic origin. According to one embodiment variant, oils of silicone origin are preferred.

For the purposes of the present invention, the term "non-volatile oil" means an oil with a vapour pressure of less than 0.13 Pa.

For the purposes of the present invention, the term "silicone oil" means an oil comprising at least one silicon atom, and especially at least one Si—O group.

The term "fluoro oil" means an oil comprising at least one fluorine atom.

The term "hydrocarbon-based oil" means an oil mainly containing hydrogen and carbon atoms.

The oils may optionally comprise oxygen, nitrogen, sulfur and/or phosphorus atoms, for example in the form of hydroxyl or acid radicals.

For the purposes of the invention, the term "volatile oil" means any oil that is capable of evaporating on contact with the skin in less than one hour, at room temperature and atmospheric pressure. The volatile oil is a volatile cosmetic compound, which is liquid at room temperature, especially having a non-zero vapour pressure, at room temperature and atmospheric pressure, especially having a vapour pressure ranging from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

Volatile Oils

The volatile oils may be hydrocarbon-based oils or silicone oils.

Among the volatile hydrocarbon-based oils containing from 8 to 16 carbon atoms, mention may be made especially of branched C8-C16 alkanes, for instance C8-C16 isoalkanes (also known as isoparaffins), isododecane, isodecane, isohexadecane and, for example, the oils sold under the trade names Isopar or Permethyl, branched C8-C16 esters, for instance isohexyl neopentanoate, and mixtures thereof. Preferably, the volatile hydrocarbon-based oil is chosen from volatile hydrocarbon-based oils containing from 8 to 16 carbon atoms, and mixtures thereof, in particular from isododecane, isodecane and isohexadecane, and is in particular isohexadecane.

Mention may also be made of volatile linear alkanes comprising from 8 to 16 carbon atoms, in particular from 10 to 15 carbon atoms and more particularly from 11 to 13 carbon atoms, for instance n-dodecane (C12) and n-tetradecane (C14) sold by Sasol under the respective references Parafol 12-97 and Parafol 14-97, and also mixtures thereof, the undecane-tridecane mixture, mixtures of n-undecane (C11) and of n-tridecane (C13) obtained in Examples 1 and 2 of patent application WO 2008/155 059 from the company Cognis, and mixtures thereof.

Volatile silicone oils that may be mentioned include linear volatile silicone oils such as hexamethyldisiloxane, octamethyltrisiloxane, decamethyltetrasiloxane, tetradecamethylhexasiloxane, hexadecamethylheptasiloxane and dodecamethylpentasiloxane.

Volatile cyclic silicone oils that may be mentioned include hexamethylcyclotrisiloxane, octamethylcyclotetrasiloxane, decamethylcyclopentasiloxane, cyclohexasiloxane and dodecamethylcyclohexasiloxane, and in particular cyclohexasiloxane.

Non-Volatile Oils

The non-volatile oils may, in particular, be selected from non-volatile hydrocarbon-based, fluoro and/or silicone oils.

Non-volatile hydrocarbon-based oils that may especially be mentioned include:
- hydrocarbon-based oils of animal origin,
- hydrocarbon-based oils of plant origin, synthetic ethers containing from 10 to 40 carbon atoms, such as dicaprylyl ether,
- hydrocarbon-based oils of mineral or synthetic origin, in particular liquid paraffin or derivatives thereof, liquid petroleum jelly, naphthalene oil, polybutylenes, hydrogenated polyisobutylenes, decene/butene copolymers, polybutene/polyisobutene copolymers, polydecenes and hydrogenated polydecenes, and mixtures thereof, and preferably hydrogenated polyisobutene;
- synthetic esters, such as the oils of formula $R_1COOR_2$, in which $R_1$ represents a linear or branched fatty acid residue comprising from 1 to 40 carbon atoms and $R_2$ represents a hydrocarbon-based chain, which is especially branched, containing from 1 to 40 carbon atoms, on condition that $R_1+R_2 \geq 10$. The esters may be chosen especially from alcohol esters of fatty acids, for instance cetostearyl octanoate, isopropyl alcohol esters such as isopropyl myristate or isopropyl palmitate, ethyl palmitate, 2-ethylhexyl palmitate, isopropyl stearate, octyl stearate, hydroxylated esters, such as isostearyl lactate or octyl hydroxystearate, alkyl or polyalkyl ricinoleates, hexyl laurate, esters of neopentanoic acid, such as isodecyl neopentanoate or isotridecyl neopentanoate, or esters of isononanoic acid, such as isononyl isononanoate or isotridecyl isononanoate, polyol esters and pentaerythritol esters, for instance dipentaerythritol tetrahydroxystearate/tetraisostearate, fatty alcohols that are liquid at room temperature, with a branched and/or unsaturated carbon-based chain containing from 12 to 26 carbon atoms, for instance 2-octyldodecanol, isostearyl alcohol and oleyl alcohol, $C_{12}$-$C_{22}$ higher fatty acids, such as oleic acid, linoleic acid and linolenic acid, and mixtures thereof, non-phenyl silicone oils, for instance caprylyl methicone, and phenyl silicone oils, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates, dimethicones or phenyl trimethicone with a viscosity of less than or equal to 100 cSt, and trimethylpentaphenyl-trisiloxane, and mixtures thereof; and also mixtures of these various oils.

A composition according to the invention may comprise from 5% to 95% by weight, better still from 10% to 70% by weight and preferably from 15% to 55% by weight of oil(s) relative to the total weight of said composition.

As mentioned above, the gelled oily phase according to the invention may have a threshold stress of greater than 1.5 Pa and preferably greater than 10 Pa. This threshold stress value reflects a gel-type texture of this oily phase.

Adjuvants

Fillers

A composition according to the invention may also comprise at least one filler, and in particular a soft-focus or haze-effect filler.

For the purposes of the present invention, the term "fillers" should be understood as meaning colourless or white solid particles of any shape, of mineral or organic, natural or synthetic nature, which are in a form that is insoluble and dispersed in the medium of the composition.

Needless to say, these fillers are used in suitable contents and under suitable conditions so as not to have a negative impact on the compositions.

The soft-focus fillers that may be used in the composition according to the invention are especially characterized by a refractive index of between 1.33 and 2.

They will generally comprise or be constituted of particles with a number-average size of less than or equal to 25 µm, especially less than or equal to 20 µm, in particular less than or equal to 15 µm.

The term "number-average size" denotes the size given by the statistical particle size distribution to half the population, referred to as D50, measured using a Malvern Mastersizer.

These particles may be of any shape and may in particular be spherical or non-spherical.

Said filler(s) are totally or partly, and preferably solely, present in the gelled aqueous phase or are totally or partly, and preferably solely, present in the gelled oily phase. Preferably, they are present in the gelled aqueous phase.

In particular, the filler is chosen from powders of crosslinked elastomeric organopolysiloxane coated with silsesquioxane resin, powders of crosslinked elastomeric organopolysiloxane coated with hydrophilic silicone resin, polytetrafluoroethylene powders, polyurethane powders, carnauba microwaxes, microwaxes of synthetic wax, silicone resin powders, hollow hemispherical silicone particles, acrylic copolymer powders, expanded vinylidene/acrylonitrile/methylene methacrylate microspheres, polyethylene powders, especially comprising at least one ethylene/acrylic acid copolymer, polymethyl methacrylate powders, powders of crosslinked elastomeric organopolysiloxane, powders of crosslinked elastomeric organopolysiloxane coated with silicone resin, starch powders, polyamide powders, silica and silicate powders, especially alumina powders, hydrophobic aerogel particles, talc with a number-average size of less than or equal to 3 microns, silica/$TiO_2$ composites, barium sulfate particles, boron nitride particles, silica particles 1 to 2% surface-treated with a mineral wax, amorphous silica microspheres, silica microbeads, talc/$TiO_2$/alumina/silica composite powders, silicone elastomers, spherical cellulose beads, and mixtures thereof.

According to a particularly advantageous embodiment of the invention, the filler is a silicone filler, preferably a powder of crosslinked elastomeric organopolysiloxane coated with silsesquioxane resin.

The powder of crosslinked elastomeric organopolysiloxane coated with hydrophilic silicone resin is generally referred to as "hydrophilic-treated", i.e. treated to render it hydrophilic.

Advantageously, to render hydrophilic the powder of crosslinked elastomeric organopolysiloxane coated with silicone resin, it is subjected to a treatment intended to combine therewith at least one cationic polymer and advantageously at least one nonionic or cationic surfactant. The cationic polymer optionally with the surfactant(s) and the powder of crosslinked elastomeric organopolysiloxane may be combined via chemical bonds or via interactions, especially via Van der Waals bonds.

In particular, the hydrophilic-treated powder of crosslinked elastomeric organopolysiloxane coated with silicone resin is combined with at least one cationic polymer, preferably a quaternary ammonium polymer, especially a polymer of INCI name "Polyquaternium" and optionally with at least one ester of $C_8$-$C_{22}$ fatty acid and of polyol which is polyoxyethylenated, preferably with 2 to 20 mol of OE, such as $C_8$-$C_{18}$ fatty acid esters of glycerol polyoxyethylenated with 3 to 15 mol of OE, preferably a polyoxyethylenated $C_8$-$C_{18}$ glycol ester, more preferentially an ester of $C_8$-$C_{18}$ fatty acid and of glycerol polyoxyethylenated with 5 to 10 mol of OE.

According to one embodiment, the hydrophilic-treated powder of crosslinked elastomeric organopolysiloxane coated with silicone resin according to the invention is combined with at least one quaternary ammonium polymer, preferably chosen from Polyquaternium-6 and Polyquaternium-7, preferentially Polyquaternium-7. Polyquaternium-6 is a poly-(diallyldimethylammonium chloride). Polyquaternium-7 is a copolymer of acrylamide and of diallyldimethylammonium chloride.

Advantageously, the powder of crosslinked elastomeric organopolysiloxane coated with silsesquioxane resin used as filler in the compositions according to the invention corresponds to the INCI name: vinyl dimethicone/methicone silsesquioxane crosspolymer and is especially the product sold under the reference KSP-100 by the company Shin-Etsu.

Advantageously, the hydrophilic-treated powder of crosslinked elastomeric organopolysiloxane coated with silicone resin, used as filler in the compositions according to the invention, corresponds to the INCI name vinyl dimethicone/methicone silsesquioxane crosspolymer treated with PEG-7 glyceryl cocoate, Polyquaternium-7 and methylsilanol tri-PEG-8 glyceryl cocoate and is especially the product sold under the reference MW-SRP-100 by the company Miyoshi Kasei.

According to an embodiment variant, a composition according to the invention may comprise from 0.2% to 40% by weight, especially from 0.5% to 37% by weight, in particular from 2% to 15% by weight of filler(s), and in particular of powder of crosslinked elastomeric organopolysiloxane coated with silicone resin, in particular of vinyl dimethicone/methicone silsesquioxane crosspolymer, relative to the total weight of said composition.

Fillers of this type are particularly advantageous insofar as they can produce a soft-focus effect on imperfections. As indicated previously, the performance of these fillers is advantageously increased by using them in a composition according to the invention.

The soft-focus effect is characterized by haze and transparency measurements (TH transmission). The "haze" corresponds to the percentage of light scattered relative to the total transmittance according to the standard ASTM D 1003 (Standard test method for haze and luminous transmittance of transparent plastics).

25 μm films of composition are applied to 50 μm polyethylene (PE) films. The film is then measured after drying for one hour at room temperature. Finally, the film is placed in the machine and transparency and haze measurements are taken.

According to a particular embodiment, in a composition according to the invention, the filler(s) are different from the oily gelling agent(s).

According to another particular embodiment, in a composition according to the invention, the filler(s) are identical to the oily gelling agent(s).

Advantageously, a composition according to the invention may comprise, besides one or more abovementioned fillers, one or more fillers conventionally used in care and/or makeup compositions.

These additional fillers are colourless or white, solid particles of any shape, which are in a form that is insoluble and dispersed in the medium of the composition.

These fillers, of mineral or organic, and natural or synthetic nature, can give the composition containing them softness, a matt effect and uniformity to the makeup.

In particular, such additional fillers may be present in a composition according to the invention in a content of between 0.5% and 10% by weight, especially between 0.5% and 7% by weight, in particular between 0.5% and 5% by weight, relative to the total weight of the composition.

According to one embodiment of the invention, a composition may also comprise at least solid particles such as pigments and/or fillers.

Advantageously, a composition according to the invention may comprise from 0.01% to 45% by weight, especially from 0.1% to 40% by weight, in particular from 1% to 35% by weight and preferably from 2% to 30% by weight of solid particles, relative to the total weight of the composition.

Dyestuffs

A composition according to the invention may also comprise at least one particulate or non-particulate, water-soluble or water-insoluble dyestuff, preferably in a proportion of at least 0.01% by weight relative to the total weight of the composition.

For obvious reasons, this amount is liable to vary significantly with regard to the desired intensity of the colour effect and the colour intensity afforded by the dyestuffs under consideration, and adjustment of said amount clearly falls within the competence of a person skilled in the art.

A composition according to the invention may comprise from 0.01% to 25% by weight, especially from 0.1% to 25% by weight, in particular from 1% to 20% by weight and preferably from 2.5% to 15% by weight of dyestuffs, relative to the total weight of said composition.

As mentioned above, the dyestuffs that are suitable for use in the invention may be water-soluble, but also liposoluble.

For the purposes of the invention, the term "water-soluble dyestuff" means any natural or synthetic, generally organic compound, which is soluble in an aqueous phase or water-miscible solvents and which is capable of colouring.

As water-soluble dyes that are suitable for use in the invention, mention may be made in particular of synthetic or natural water-soluble dyes, for instance FDC Red 4, DC Red 6, DC Red 22, DC Red 28, DC Red 30, DC Red 33, DC Orange 4, DC Yellow 5, DC Yellow 6, DC Yellow 8, FDC Green 3, DC Green 5, FDC Blue 1, betanine (beetroot), carmine, copper chlorophylline, methylene blue, anthocyanins (enocianin, black carrot, hibiscus and elder), caramel and riboflavin.

The water-soluble dyes are, for example, beetroot juice and caramel.

For the purposes of the invention, the term "liposoluble dyestuff" means any natural or synthetic, generally organic compound, which is soluble in an oily phase or solvents that are miscible with a fatty substance and which is capable of colouring.

As liposoluble dyes that are suitable for use in the invention, mention may be made especially of synthetic or natural liposoluble dyes, for instance DC Red 17, DC Red 21, DC Red 27, DC Green 6, DC Yellow 11, DC Violet 2, DC Orange 5, Sudan red, carotenes (β-carotene, lycopene), xanthophylls (capsanthin, capsorubin, lutein), palm oil, Sudan brown, quinoline yellow, annatto and curcumin.

The colouring particulate materials may be present in a proportion of from 0.01% to 15% by weight, relative to the total weight of the composition containing them.

They may especially be pigments, nacres and/or particles with metallic glints.

The term "pigments" should be understood as meaning white or coloured, mineral or organic particles, which are insoluble in an aqueous solution, and which are intended to colour and/or opacify the composition containing them.

A composition according to the invention may comprise from 0.01% to 25% by weight, especially from 0.1% to 25% by weight, in particular from 1% to 25% by weight and preferably from 2.5% to 15% by weight of pigments, relative to the total weight of said composition.

Preferably, when the composition according to the invention is a makeup composition, it may comprise at least 2.5% and preferentially at least 10% by weight of pigments, relative to the total weight of said composition.

The pigments may be white or coloured, and mineral and/or organic.

As mineral pigments that may be used in the invention, mention may be made of titanium, zirconium or cerium oxides or dioxides, and also zinc, iron or chromium oxides, ferric blue, manganese violet, ultramarine blue and chromium hydrate, and mixtures thereof.

It may also be a pigment having a structure that may be, for example, of sericite/brown iron oxide/titanium dioxide/silica type. Such a pigment is sold, for example, under the reference Coverleaf NS or JS by the company Chemicals and Catalysts, and has a contrast ratio in the region of 30.

They may also be pigments having a structure that may be, for example, of silica microsphere type containing iron oxide. An example of a pigment having this structure is the product sold by the company Miyoshi under the reference PC Ball PC-LL-100 P, this pigment consisting of silica microspheres containing yellow iron oxide.

Advantageously, the pigments in accordance with the invention are iron oxides and/or titanium dioxides.

The term "nacres" should be understood as meaning iridescent or non-iridescent coloured particles of any shape, especially produced by certain molluscs in their shell or alternatively synthesized, which have a colour effect via optical interference.

A composition according to the invention may comprise from 0% to 15% by weight of nacres relative to the total weight of said composition.

The nacres may be chosen from nacreous pigments such as titanium mica coated with an iron oxide, titanium mica coated with bismuth oxychloride, titanium mica coated with chromium oxide, titanium mica coated with an organic dye and also nacreous pigments based on bismuth oxychloride. They may also be mica particles at the surface of which are superimposed at least two successive layers of metal oxides and/or of organic dyestuffs.

Examples of nacres that may also be mentioned include natural mica coated with titanium oxide, with iron oxide, with natural pigment or with bismuth oxychloride.

Among the nacres available on the market, mention may be made of the nacres Timica, Flamenco and Duochrome (based on mica) sold by the company Engelhard, the Timiron nacres sold by the company Merck, the Prestige mica-based nacres sold by the company Eckart, and the Sunshine synthetic mica-based nacres sold by the company Sun Chemical.

The nacres may more particularly have a yellow, pink, red, bronze, orange, brown, gold and/or coppery colour or glint.

Advantageously, the nacres in accordance with the invention are micas covered with titanium dioxide or with iron oxide, and also bismuth oxychloride.

For the purposes of the present invention, the term "particles with a metallic glint" means any compound whose nature, size, structure and surface finish allow it to reflect the incident light, especially in a non-iridescent manner.

The particles with a metallic glint that may be used in the invention are in particular chosen from:
  particles of at least one metal and/or of at least one metal derivative;
  particles comprising a monomaterial or multimaterial organic or mineral substrate, at least partially coated with at least one layer with a metallic glint comprising at least one metal and/or at least one metal derivative, and
  mixtures of said particles.

Among the metals that may be present in said particles, mention may be made, for example, of Ag, Au, Cu, Al, Ni, Sn, Mg, Cr, Mo, Ti, Zr, Pt, Va, Rb, W, Zn, Ge, Te and Se, and mixtures or alloys thereof Ag, Au, Cu, Al, Zn, Ni, Mo and Cr, and mixtures or alloys thereof (for example bronzes and brasses) are preferred metals.

The term "metal derivatives" denotes compounds derived from metals, especially oxides, fluorides, chlorides and sulfides.

Illustrations of these particles that may be mentioned include aluminium particles, such as those sold under the names Starbrite 1200 EAC® by the company Siberline and Metalure® by the company Eckart and glass particles coated with a metallic layer, in particular those described in documents JP-A-09188830, JP-A-10158450, JP-A-10158541, JP-A-07258460 and JP-A-05017710.

Hydrophobic Treatment of the Dyestuffs

The pulverulent dyestuffs as described previously may be totally or partially surface-treated with a hydrophobic agent, to make them more compatible with the oily phase of the composition of the invention, especially so that they have good wettability with oils. Thus, these treated pigments are well dispersed in the oily phase.

Hydrophobic-treated pigments are especially described in EP-A-1086683.

The hydrophobic-treatment agent may be chosen from silicones such as methicones, dimethicones and perfluoroalkylsilanes; fatty acids, such as stearic acid; metal soaps, such as aluminium dimyristate, the aluminium salt of hydrogenated tallow glutamate; perfluoroalkyl phosphates, polyhexafluoropropylene oxides; perfluoropolyethers; amino acids; N-acylamino acids or salts thereof lecithin, isopropyl triisostearyl titanate, isostearyl sebacate, and mixtures thereof.

The term "alkyl" mentioned in the compounds mentioned previously especially denotes an alkyl group containing from 1 to 30 carbon atoms and preferably containing from 5 to 16 carbon atoms.

Polar Additives

Advantageously, a composition according to the invention may also comprise one or more polar additives.

According to the present invention, the use of such a polar additive may in particular facilitate the homogenization of the dispersion in the presence of pigments.

The polar additive may be chosen from compounds considered as good hydrogen bond donors or acceptors, for instance fatty alcohols, fatty acids, diols and esters, and mixtures thereof.

According to one embodiment, the polar additives of the invention may be polar oils.

According to one embodiment, the polar additives of the invention may be amphiphilic compounds, comprising a lipophilic part connected to a polar part, for example chosen from esters, C12 to C26 branched fatty alcohols such as octyldodecanol, or amphiphilic silicone compounds. The polar additives of the invention may also be agents for screening out UV-B and/or UV-A rays, the total amount of screening agent possibly being between 0.01% and 10% by weight relative to the total weight of the composition.

A composition according to the invention may comprise from 0.01% to 10% by weight, especially from 0.05% to 5% by weight and in particular from 0.05% to 1% by weight of polar additive(s).

Active Agents

A composition according to the invention may comprise at least one moisturizer (also known as a humectant), in particular for a care application.

Preferably, the moisturizer is glycerol.

The moisturizer(s) may be present in the composition in a content ranging from 0.1% to 15% by weight, especially from 0.5% to 10% by weight or even from 1% to 6% by weight relative to the total weight of said composition.

As other active agents that may be used in the composition of the invention, examples that may be mentioned include vitamins, sunscreens, and mixtures thereof, and in particular vitamins such as tocopherol.

Preferably, a composition according to the invention comprises at least one active agent, in particular chosen from moisturizers, preferably glycerol, vitamins, preferably tocopherol, and mixtures thereof.

According to a preferred embodiment, a composition according to the invention additionally comprises at least one active agent.

Preferably, the active agent is chosen from shea butter and sodium hyaluronate, and a mixture thereof.

In addition, a composition according to the invention may comprise at least one dispersant.

It is a matter of routine operations for a person skilled in the art to adjust the natures and the amounts of the additives present in the compositions in accordance with the invention so that the cosmetic properties desired for the latter are not affected thereby.

According to a preferred embodiment, a composition of the invention may advantageously be in the form of a composition for caring for the skin and/or keratin fibres, the body or the face, in particular the face.

In particular, a composition of the invention may advantageously be in the form of an anti-ageing care composition for the skin of the body or the face, in particular the face.

According to another embodiment, a composition of the invention may advantageously be in the form of a composition for making up the skin and/or keratin fibres, the body or the face, in particular the face.

Thus, according to a sub-mode of this embodiment, a composition of the invention may advantageously be in the form of a makeup base composition for makeup. A composition of the invention may advantageously be in the form of a foundation.

According to another sub-mode of this embodiment, a composition of the invention may advantageously be in the form of a composition for making up the skin and in particular the face. It may thus be an eyeshadow or a face powder.

According to yet another sub-mode of this embodiment, a composition of the invention may advantageously be in the form of a product for the lips, in particular a lipstick.

According to yet another sub-mode of this embodiment, 2 composition of the invention may be in the form of a product for the eyelashes, in particular 2 mascara.

According to yet another sub-mode of this embodiment, a composition of the invention may advantageously be in the form of a product for the eyebrows, in particular an eyebrow pencil.

Such compositions are prepared in particular according to the general knowledge of a person skilled in the art.

Throughout the description, including the claims, the term "comprising a" should be understood as being synonymous with "comprising at least one", unless otherwise specified.

The terms "between . . . and . . . ", "comprises from . . . to . . . ", "formed from . . . to . . . ", and "ranging from . . . to . . . " should be understood as being inclusive of the limits, unless otherwise specified.

The invention is illustrated in more detail by the examples presented below. Unless otherwise indicated, the amounts shown are expressed as percentages by weight.

Methodology for the Oscillating Dynamic Rheology Measurements

These are harmonic-regime rheology measurements for measuring the elastic modulus.

The measurements are taken using a Haake RS600 rheometer on a product at rest, at 25° C. with a plate-plate rotor Ø 60 mm and a 2 mm gap.

The harmonic-regime measurements make it possible to characterize the viscoelastic properties of the products. The technique consists in subjecting a material to a stress which varies sinusoidally over time and in measuring the response of the material to this stress. In a range in which the behaviour is linear viscoelastic behaviour (zone in which the strain is proportional to the stress), the stress ($\tau$) and the strain ($\gamma$) are two sinusoidal functions of time which are written in the following manner:

$$\tau(t) = \tau_0 \sin(\omega t)$$

$$\gamma(t) = \gamma_0 \sin(\omega t + \delta)$$

in which:
$\tau_0$ represents the maximum amplitude of the stress (Pa);
$\gamma_0$ represents the maximum amplitude of the strain (–);
$\omega = 2\Pi N$ represents the angular frequency (rad·s$^{-1}$) with N representing the frequency (Hz); and
$\delta$ represents the phase shift of the stress relative to the strain (rad).

Thus, the two functions have the same angular frequency, but they are shifted by an angle $\delta$. Depending on the phase shift $\delta$ between $\tau(t)$ and $\gamma(t)$, the behaviour of the system may be apprehended:
if $\delta = 0$, the material is purely elastic;
if $\delta = \Pi/2$, the material is purely viscous (Newtonian fluid); and
if $0 < \delta < \Pi/2$, the material is viscoelastic.

In general, the stress and the strain are written in complex form:

$$\tau^*(t) = \tau_0 e^{i\omega t}$$

$$\gamma^*(t) = \gamma_0 e^{(i\omega t + \delta)}$$

A complex stiffness modulus, representing the overall resistance of the material to the strain, whether it is of elastic or viscous origin, is then defined by:

$$G^* = \tau^*/\gamma^* = G' + iG''$$

in which:
G' is the storage modulus or elastic modulus, which characterizes the energy stored and totally restituted during a cycle, $G' = (\tau_0/\gamma_0) \cos \delta$; and
G" is the loss modulus or viscous modulus, which characterizes the energy dissipated by internal friction during a cycle, $G'' = (\tau_0/\gamma_0) \sin \delta$.

The parameter retained is the mean stiffness modulus G* recorded at the plateau measured at a frequency of 1 Hz.

EXAMPLES

Measurement Methods

In the examples detailed below, the following measurement methods are used.

Measurement of the Soft Focus

The soft focus is determined by measuring the haze and the transparency, i.e. the perception of light at wide angles.

The measurements are taken using a Hazegard (Hazegard Plus C©, Byk-Gardner) on a film 50 μm thick, deposited on a PET film (PA-2871©, Byk-Gardner). 3 measurements are taken after drying for 1 hour at room temperature.

Measurement of the Tack and the Glidance

The performance qualities in terms of glidance and tack are determined by means of a SWIFT evaluation by a panel of 2 trained and competent people.

Visual Effect

The evaluation of the visual effect consists in grading the performance level according to two criteria: masking and matt effect, from 1 (less effect) to 5.5 (more effect) on a Skin FX support (CLSFX, reference SKINFX-DS8-H40-MLT-CST+CBW) and compared by reference points.

Sensory Effect

The evaluation of the sensory effect consists in grading the performance level according to three criteria: application, playtime and feel, from 1 (less effect) to 5.5 (more effect) on a Skin FX support sheet (CLSFX, reference SKINFX-SH-H40-BAK-COULEUR-LAN) applied to the back of the hand.

Example 1

The care compositions 1 (according to the invention) and 2 (outside the invention) were prepared and their cosmetic properties were evaluated.

1) Preparation of Composition 1 According to the Invention

A composition 1 in accordance with the invention is prepared.

Prior to the preparation of the composition, a solid composition A formed from the following ingredients is prepared:

| Composition A | Content (weight %) |
|---|---|
| Cetearyl ethylhexanoate (and) isopropyl myristate (Dub Liquide 85 IP ®, Stéarineries Dubois) | 23.33 |
| Hydrogenated polyisobutene (Parleam ®, NOF Corporation) | 23.33 |
| Mineral oil (Marcol 82 ®, Exxonmobil Chemical) | qs 100 |
| Glyceryl dibehenate (53%) (and) tribehenin (30%) (and) glyceryl behenate (17%) (Compritol 888 CG ATO ®, Gattefossé) | 30 |

The composition is prepared in a continuous twin-screw blender, such as the BC-21 model from the company Clextral, and is performed under the following conditions:

inlet temperature: 80° C.;

outlet temperature: 20° C.;

flow rate: 3 kg/hour; and screw speed: 600 rpm.

The pre-melted waxes are introduced into the top of the blender, at the same time as the oil, and the mixture is then cooled with continuous twin-screw blending down to the outlet temperature.

An organopolysiloxane powder composition 1 according to the invention as detailed in the table below is prepared.

The lipophilic phase is prepared beforehand.

The lipophilic phase and composition A are homogenized in a Rayneri blender for the purposes of dispersing composition A in the form of solid aggregates.

The hydrophilic phase is prepared and then added at room temperature to the lipophilic phase and to the solid aggregates of composition A.

| Phase | Composition 1 according to the invention | Content (weight %) |
|---|---|---|
| Hydrophilic phase | Water | qs 100 |
| | Glycerol | 15.00 |
| | Adenosine | 0.10 |
| | Phenoxyethanol | 0.50 |
| | Disodium EDTA | 0.20 |
| | Sodium hyaluronate (Cristalhyal LO ®, Soliance) | 0.10 |
| | Hydroxyethyl acrylate/sodium acryloyldimethyltaurate copolymer (Sepinov EMT 10 ®, SEPPIC) | 1.35 |
| | Vinyl dimethicone/methicone silsesquioxane crosslinked polymer (KSP-100 ®, Shin-Etsu) | 4.55 |
| | Boron nitride (Boron Nitride Powder Tres BN PUHP 3002 ®, Saint-Gobain Ceramics) | 0.65 |
| Aggregates Lipophilic phase | Dispersion of solid aggregates of composition A | 23 |
| | Isopropyl lauroyl sarcosinate (Eldew SL-205 ®, Ajinomoto) | 0.90 |
| | Dimethicone (KF-96L-2CS ®, Shin-Etsu) | 2.40 |
| | Caprylyl glycol | 0.20 |
| | Dimethicone (and) dimethicone/vinyl dimethicone crosspolymer (X-25-7034H ®, Shin-Etsu) | 9.00 |
| | Shea butter (Lipex 204 TR ®, Aarhuskarlshamn) | 2.00 |
| | Synthetic fluorphlogopite (and) titanium dioxide (and) iron oxides (and) tin oxide | 0.10 |
| | Titanium dioxide (and) mica | 0.15 |
| | Fragrance | 0.10 |

2) Preparation of Composition 2 Outside the Invention

A composition 2 outside the invention is prepared using the following weight proportions:

| Phases | Composition 2 outside the invention | Content (weight %) |
|---|---|---|
| Hydrophilic phase | Water | qs 100 |
| | Glycerol | 15.00 |
| | Adenosine | 0.10 |

-continued

| Phases | Composition 2 outside the invention | Content (weight %) |
|---|---|---|
| | Phenoxyethanol | 0.50 |
| | Disodium EDTA | 0.20 |
| | Sodium hyaluronate (Cristalhyal LO ®, Soliance) | 0.10 |
| | Hydroxyethyl acrylate/sodium acryloyldimethyltaurate copolymer (Sepinov EMT 10 ®, SEPPIC) | 1.35 |
| | Vinyl dimethicone/methicone silsesquioxane crosslinked polymer (KSP-100 ®, Shin-Etsu) | 4.55 |
| | Boron nitride (Boron Nitride Powder Tres BN PUHP 3002 ®, Saint-Gobain Ceramics) | 0.65 |
| Lipophilic phase | Cetearyl ethylhexanoate (and) isopropyl myristate (Dub Liquide 85 IP ®, Stéarineries Dubois) | 5.37 |
| | Hydrogenated polyisobutene (Parleam ®, NOF Corporation) | 5.37 |
| | Mineral oil (Marcol 82 ®, Exxonmobil Chemical) | 5.37 |
| | Glyceryl dibehenate (and) tribehenin (and) glyceryl behenate (Compritol 888 CG ATO ®, Gattefossé) | 6.90 |
| | Isopropyl lauroyl sarcosinate (Eldew SL-205 ®, Ajinomoto) | 0.90 |
| | Dimethicone (KF-96L-2CS ®, Shin-Etsu) | 2.40 |
| | Caprylyl glycol | 0.20 |
| | Dimethicone (and) dimethicone/vinyl dimethicone crosspolymer (X-25-7034H ®, Shin-Etsu) | 9.00 |
| | Shea butter (Lipex 204 TR ®, Aarhuskarlshamn) | 2.00 |
| | Synthetic fluorphlogopite (and) titanium dioxide (and) iron oxides (and) tin oxide | 0.10 |
| | Titanium dioxide (and) mica | 0.15 |
| | Fragrance | 0.10 |

Each hydrophilic and lipophilic phase is prepared beforehand. The components are weighed out, heated with Rayneri blender at 80° C. and then cooled without stirring. The hydrophilic and lipophilic phases are homogenized together with Rayneri blender at room temperature.

3) Evaluation of the Cosmetic Properties

Composition 1 in accordance with the invention, comprising a dispersion of solid aggregates, has better masking performance with provision of sheen and also better performance qualities in terms of glidance and tack (ease of application, and skin less tacky), compared with composition 2 outside the invention.

The soft-focus results are presented in the table below:

| Composition | Haze (%) | Transmittance (%) |
|---|---|---|
| 1 | 79 ± 0.3 | 87.1 ± 0.3 |
| 2 | 54.2 ± 0.3 | 89.5 ± 0.3 |

Composition 1 in accordance with the invention comprising a dispersion of solid aggregates has better soft-focus performance than composition 2 outside the invention.

Furthermore, composition 1 according to the invention exhibits a reduced fluffing effect during the application compared to composition 2 outside the invention.

Example 2

The care compositions 3, 5 and 7 (according to the invention) and 4 and 6 (outside the invention) were prepared and their cosmetic properties were evaluated.

1) Preparation of Composition 3 According to the Invention

Prior to the preparation of the composition, a solid composition B formed from the following ingredients is prepared according to the protocol indicated in Example 1 for composition A.

| Composition B | Content (weight %) |
|---|---|
| Cetearyl ethylhexanoate (and) isopropyl myristate (Dub Liquide 85 IP ®, Stéarineries Dubois) | 23.33 |
| Hydrogenated polyisobutene (Parleam ®, NOF Corporation) | 23.33 |
| Mineral oil (Marcol 82 ®, Exxonmobil Chemical) | qs 100 |
| Glyceryl dibehenate (and) tribehenin (and) glyceryl behenate (Compritol 888 CG ATO ®, Gattefossé) | 30 |

A composition 3 according to the invention as detailed in the table below is prepared, according to the same protocol used for composition 1 of Example 1:

| Phase | Composition 3 according to the invention | Content (weight %) |
|---|---|---|
| Hydrophilic phase | Water | qs 100 |
| | Glycerol | 18.45 |
| | Adenosine | 0.10 |
| | Phenoxyethanol | 0.50 |
| | Disodium EDTA | 0.20 |
| | Sodium hyaluronate (Cristalhyal LO ®, Soliance) | 0.10 |
| | Hydroxyethyl acrylate/sodium acryloyldimethyltaurate copolymer (Sepinov EMT 10 ®, SEPPIC) | 1.69 |

| Phase | Composition 3 according to the invention | Content (weight %) |
| --- | --- | --- |
| | Vinyl dimethicone/methicone silsesquioxane crosslinked polymer (KSP-100 ®, Shin-Etsu) | 5.95 |
| | Boron nitride (Boron Nitride Powder Tres BN PUHP 3002 ®, Saint-Gobain Ceramics) | 0.85 |
| Aggregates | Dispersion of solid aggregates of composition B | 7.5 |
| Lipophilic phase | Isopropyl lauroyl sarcosinate (Eldew SL-205 ®, Ajinomoto) | 0.38 |
| | Dimethicone (KF-96L-2CS ®, Shin-Etsu) | 1.58 |
| | Caprylyl glycol | 0.20 |
| | Dimethicone (and) dimethicone/vinyl dimethicone crosspolymer (X-25-7034H ®, Shin-Etsu) | 5.48 |
| | Capryloylsalicylic acid | 0.3 |
| | Shea butter (Lipex 204 TR ®, Aarhuskarlshamn) | 2.00 |

2) Preparation of Composition 4 Outside the Invention

A composition 4 outside the invention is prepared using the following weight proportions, according to the same protocol used for composition 2 of Example 1:

| Phases | Composition 4 outside the invention | Content (weight %) |
| --- | --- | --- |
| Hydrophilic phase | Water | qs 100 |
| | Glycerol | 18.45 |
| | Adenosine | 0.10 |
| | Phenoxyethanol | 0.50 |
| | Disodium EDTA | 0.20 |
| | Sodium hyaluronate (Cristalhyal LO ®, Soliance) | 0.10 |
| | Hydroxyethyl acrylate/sodium acryloyldimethyltaurate copolymer (Sepinov EMT 10 ®, SEPPIC) | 1.69 |
| | Vinyl dimethicone/methicone silsesquioxane crosslinked polymer (KSP-100 ®, Shin-Etsu) | 5.95 |
| | Boron nitride (Boron Nitride Powder Tres BN PUHP 3002 ®, Saint-Gobain Ceramics) | 0.85 |
| Lipophilic phase | Cetearyl ethylhexanoate (and) isopropyl myristate (Dub Liquide 85 IP ®, Stéarineries Dubois) | 1.75 |
| | Hydrogenated polyisobutene (Parleam ®, NOF Corporation) | 1.75 |
| | Mineral oil (Marcol 82 ®, Exxonmobil Chemical) | 1.75 |
| | Glyceryl dibehenate (and) tribehenin (and) glyceryl behenate (Compritol 888 CG ATO ®, Gattefossé) | 2.25 |
| | Isopropyl lauroyl sarcosinate (Eldew SL-205 ®, Ajinomoto) | 0.38 |
| | Dimethicone (KF-96L-2CS ®, Shin-Etsu) | 1.58 |
| | Caprylyl glycol | 0.20 |
| | Dimethicone (and) dimethicone/vinyl dimethicone crosspolymer (X-25-7034H ®, Shin-Etsu) | 5.48 |
| | Capryloylsalicylic acid | 0.3 |
| | Shea butter (Lipex 204 TR ®, Aarhuskarlshamn) | 2.00 |

3) Preparation of Composition 5 According to the Invention

Prior to the preparation of the composition, a solid composition C formed from the following ingredients is prepared according to the protocol indicated in Example 1 for composition A.

| Composition C | Content (weight %) |
| --- | --- |
| Cetearyl ethylhexanoate (and) isopropyl myristate (Dub Liquide 85 IP ®, Stéarineries Dubois) | 20 |
| Hydrogenated polyisobutene (Parleam ®, NOF Corporation) | 20 |
| Mineral oil (Marcol 82 ®, Exxonmobil Chemical) | qs 100 |
| Beeswax | 40 |

A composition 5 according to the invention as detailed in the table below is prepared, according to the same protocol used for composition 1 of Example 1:

| Phase | Composition 5 according to the invention | Content (weight %) |
|---|---|---|
| Hydrophilic phase | Water | qs 100 |
| | Glycerol | 11.05 |
| | Phenoxyethanol | 0.50 |
| | Disodium EDTA | 0.20 |
| | Hydroxyethyl acrylate/sodium acryloyldimethyltaurate copolymer (Sepinov EMT 10 ®, SEPPIC) | 1.11 |
| | Vinyl dimethicone/methicone silsesquioxane crosslinked polymer (KSP-100 ®, Shin-Etsu) | 4.55 |
| | Boron nitride (Boron Nitride Powder Tres BN PUHP 3002 ®, Saint-Gobain Ceramics) | 0.65 |
| Aggregates | Dispersion of solid aggregates of composition C | 23 |
| Lipophilic phase | Isopropyl lauroyl sarcosinate (Eldew SL-205 ®, Ajinomoto) | 0.6 |
| | Dimethicone (KF-96L-2CS ®, Shin-Etsu) | 2.52 |
| | Caprylyl glycol | 0.20 |
| | Dimethicone (and) dimethicone/vinyl dimethicone crosspolymer (X-25-7034H ®, Shin-Etsu) | 8.76 |

4) Preparation of Composition 6 Outside the Invention

A composition 6 outside the invention is prepared using the following weight proportions, according to the same protocol used for composition 2 of Example 1:

| | Composition 6 outside the invention | Content (weight %) |
|---|---|---|
| Hydrophilic phase | Water | qs 100 |
| | Glycerol | 11.05 |
| | Phenoxyethanol | 0.50 |
| | Disodium EDTA | 0.20 |
| | Hydroxyethyl acrylate/sodium acryloyldimethyltaurate copolymer (Sepinov EMT 10 ®, SEPPIC) | 1.11 |
| | Vinyl dimethicone/methicone silsesquioxane crosslinked polymer (KSP-100 ®, Shin-Etsu) | 4.55 |
| | Boron nitride (Boron Nitride Powder Tres BN PUHP 3002 ®, Saint-Gobain Ceramics) | 0.65 |
| Lipophilic phase | Cetearyl ethylhexanoate (and) isopropyl myristate (Dub Liquide 85 IP ®, Stéarineries Dubois) | 4.6 |
| | Hydrogenated polyisobutene (Parleam ®, NOF Corporation) | 4.6 |
| | Mineral oil (Marcol 82 ®, Exxonmobil Chemical) | 4.6 |
| | Beeswax | 9.2 |
| | Isopropyl lauroyl sarcosinate (Eldew SL-205 ®, Ajinomoto) | 0.6 |
| | Dimethicone (KF-96L-2CS ®, Shin-Etsu) | 2.52 |
| | Caprylyl glycol | 0.20 |
| | Dimethicone (and) dimethicone/vinyl dimethicone crosspolymer (X-25-7034H ®, Shin-Etsu) | 8.76 |

5) Preparation of Composition 7 According to the Invention

Prior to the preparation of the composition, a solid composition D formed from the following ingredients is prepared according to the protocol indicated in Example 1 for composition A.

| Composition D | Content (weight %) |
|---|---|
| Cetearyl ethylhexanoate (and) isopropyl myristate (Dub Liquide 85 IP ®, Stéarineries Dubois) | 23.33 |
| Hydrogenated polyisobutene (Parleam ®, NOF Corporation) | 23.33 |
| Mineral oil (Marcol 82 ®, Exxonmobil Chemical) | qs 100 |
| Glyceryl dibehenate (and) tribehenin (and) glyceryl behenate (Compritol 888 CG ATO ®, Gattefossé) | 30 |

A composition 7 according to the invention as detailed in the table below is prepared, according to the same protocol used for composition 1 of Example 1:

| Phase | Composition 7 according to the invention | Content (weight %) |
|---|---|---|
| Hydrophilic phase | Water | qs 100 |
| | Glycerol | 16.92 |
| | Adenosine | 0.10 |
| | Phenoxyethanol | 0.50 |
| | Disodium EDTA | 0.20 |
| | Sodium hyaluronate (Cristalhyal LO ®, Soliance) | 0.10 |
| | Hydroxyethyl acrylate/sodium acryloyldimethyltaurate copolymer (Sepinov EMT 10 ®, SEPPIC) | 1.30 |
| | Vinyl dimethicone/methicone silsesquioxane crosslinked polymer (KSP-100 ®, Shin-Etsu) | 5.32 |
| | Boron nitride (Boron Nitride Powder Tres BN PUHP 3002 ®, Saint-Gobain Ceramics) | 0.76 |
| Aggregates | Dispersion of solid aggregates of composition D | 12 |
| Lipophilic phase | Isopropyl lauroyl sarcosinate (Eldew SL-205 ®, Ajinomoto) | 0.6 |
| | Dimethicone (KF-96L-2CS ®, Shin-Etsu) | 2.52 |
| | Caprylyl glycol | 0.20 |
| | Capryloylsalicylic acid | 0.3 |
| | Dimethicone (and) dimethicone/vinyl dimethicone crosspolymer (X-25-7034H ®, Shin-Etsu) | 8.46 |
| | Shea butter (Lipex 204 TR ®, Aarhuskarlshamn) | 2.00 |
| | Synthetic fluorphlogopite (and) titanium dioxide (and) iron oxides (and) tin oxide | 0.10 |
| | Titanium dioxide (and) mica | 0.15 |
| | Fragrance | 0.15 |

6) Evaluation of the Cosmetic Properties

Compositions 3 and 5 in accordance with the invention, comprising a dispersion of solid aggregates, have better masking performance with provision of sheen and also better performance qualities in terms of glidance and tack (ease of application, and skin less tacky), compared with compositions 4 and 6 outside the invention.

In particular, compared with compositions 4 and 6, compositions 3 and 5 according to the invention allow better application and a better sensory effect. Compositions 3 and 5 are less tacky and more glidant, resulting in better playtime and greater softness.

Composition 7 according to the invention has very good emollience and comfort properties.

The soft-focus results are presented in the table below:

| Composition | Haze (%) | Transmittance (%) |
|---|---|---|
| 3 | 80.83 ± 0.3 | 88.63 ± 0.3 |
| 4 | 78.46 ± 0.3 | 87.73 ± 0.3 |
| 5 | 85.83 ± 0.3 | 89.03 ± 0.3 |
| 6 | 79.03 ± 0.3 | 88.45 ± 0.3 |

Composition 3 in accordance with the invention, comprising solid aggregates, in the form of dispersed particles, has better soft-focus performance than composition 4 outside the invention. Similarly, composition 5 has better performance qualities than composition 6.

Compared with composition 4, composition 3 according to the invention has a better measured and perceived soft-focus optical effect: the formulations are less matt. This is likewise the case for composition 5 compared with composition 6.

Furthermore, compositions 3, 5 and 7 according to the invention all exhibit a reduced fluffing effect during the application compared to compositions 4 and 6 outside the invention.

The invention claimed is:

1. A composition, comprising:
at least one aqueous phase gelled with at least one hydrophilic gelling agent; and
at least one oily phase gelled with at least one lipophilic gelling agent chosen from organopolysiloxane elastomers;
said phases forming therein a macroscopically homogeneous mixture;
wherein said composition also comprises a dispersion of solid aggregates, said aggregates being formed from 10% to 80% by weight of wax(es), relative to their total weight,
wherein said aggregates comprises:
i) cetearyl ethylhexanoate and isopropyl myristate, hydrogenated polyisobutene and a mineral oil, and glyceryl dibehenate and tribehenin and glyceryl behenate, or
ii) cetearyl ethylhexanoate and isopropyl myristate, hydrogenated polyisobutene and a mineral oil, and a beeswax, and
wherein said aggregates are an assembly of different compounds which adhere together and form a whole, and said aggregates being dispersed in the gelled oily phase.

2. The composition of claim 1, comprising from 1% to 40% by weight of solid aggregates relative to the total weight of the composition.

3. The composition of claim 1, wherein the solid aggregates are formed from 15% to 60% by weight of wax(es) relative to their total weight.

4. The composition of claim 1, wherein said aggregates have a size of between 0.1 μm and 100 μm.

5. The composition of claim 1, wherein said aggregates have, at 25° C. and under atmospheric pressure, a hardness of greater than 0.5 N.

6. The composition of claim 1, wherein the hydrophilic gelling agent is chosen from synthetic polymeric gelling agents.

7. The composition of claim 1, wherein the hydrophilic gelling agent is chosen from 2-acrylamido-2-methylpropanesulfonic acid polymers and copolymers.

8. The composition of claim 1, wherein the lipophilic gelling agent chosen from organopolysiloxane elastomers is chosen from Dimethicone Crosspolymer, Dimethicone and Dimethicone Crosspolymer, Vinyl Dimethicone Crosspolymer, Dimethicone/Vinyl Dimethicone Crosspolymer, Dimethicone and Dimethicone/Vinyl Dimethicone Crosspolymer, and Dimethicone Crosspolymer-3.

9. The composition of claim 1, wherein the gelled aqueous phase also comprises at least one filler.

10. A process for preparing a composition according to claim 1, comprising at least the following steps:
   i) providing a first solid composition comprising from 10% to 80% by weight of wax(es), relative to the total weight of the composition, and comprising at least
      a) cetearyl ethylhexanoate and isopropyl myristate, hydrogenated polyisobutene and a mineral oil, and glyceryl dibehenate and tribehenin and glyceryl behenate, or b) cetearyl ethylhexanoate and isopropyl myristate, hydrogenated polyisobutene and a mineral oil, and a beeswax, and
   ii) providing an oily phase gelled with at least one lipophilic gelling agent chosen from organopolysiloxane elastomers;
   iii) mixing said first solid composition and said gelled oily phase with stirring at room temperature, under conditions that are effective for dispersing said first composition in the form of solid aggregates in said gelled oily phase, said aggregates being an assembly of different compounds which adhere together and form a whole;
   iv) introducing into the mixture obtained on conclusion of the preceding step an aqueous phase gelled with at least one hydrophilic gelling agent, at room temperature, under conditions that are suitable for obtaining a macroscopically homogeneous mixture.

11. The process of claim 10, wherein said first solid composition of step i) is prepared at a temperature of between 30° C. and 120° C., and then cooled to room temperature.

12. A cosmetic process for making up and/or caring for keratin materials, comprising at least one step of applying to said keratin materials a composition as defined according to claim 1.

* * * * *